(12) United States Patent
Wainwright et al.

(10) Patent No.: US 7,968,280 B2
(45) Date of Patent: Jun. 28, 2011

(54) METHODS FOR THE DETECTION AND/OR QUANTIFICATION OF GRAM POSITIVE BACTERIAL CONTAMINANTS

(75) Inventors: Norman R. Wainwright, Johns Island, SC (US); Foster T. Jordan, Chapin, SC (US)

(73) Assignee: Charles River Laboratories, Inc., Wilmington, MA (US)

( * ) Notice: Subject to any disclaimer, the term of this patent is extended or adjusted under 35 U.S.C. 154(b) by 1036 days.

(21) Appl. No.: 11/292,295

(22) Filed: Dec. 1, 2005

(65) Prior Publication Data

US 2006/0183181 A1 Aug. 17, 2006

Related U.S. Application Data

(60) Provisional application No. 60/632,785, filed on Dec. 2, 2004.

(51) Int. Cl.
*C12Q 1/00* (2006.01)
*A61K 35/56* (2006.01)

(52) U.S. Cl. .......................................... 435/4; 424/538

(58) Field of Classification Search ................... 424/538
See application file for complete search history.

(56) References Cited

U.S. PATENT DOCUMENTS

| | | | |
|---|---|---|---|
| 3,915,805 A | 10/1975 | Levin | |
| 3,944,391 A | 3/1976 | Harris et al. | |
| 3,954,663 A | 5/1976 | Yamamoto et al. | |
| 4,038,029 A | 7/1977 | Teller et al. | |
| 4,038,147 A | 7/1977 | Reno | |
| 4,221,865 A | 9/1980 | Dubczak et al. | |
| 4,221,866 A | 9/1980 | Cotter | |
| 4,245,044 A | 1/1981 | Kuo et al. | |
| D258,144 S | 2/1981 | Kallet et al. | |
| 4,273,557 A | 6/1981 | Juranas | |
| 4,279,774 A | 7/1981 | Lindsay et al. | |
| 4,301,245 A | 11/1981 | Lindsay et al. | |
| 4,322,217 A | 3/1982 | Dikeman | |
| 4,370,413 A | 1/1983 | Neeman et al. | |
| 4,376,819 A | 3/1983 | Brown et al. | |
| D278,182 S | 3/1985 | Aihara et al. | |
| 4,606,824 A | 8/1986 | Chu et al. | |
| 4,717,658 A | 1/1988 | Michaels | |
| 4,806,316 A | 2/1989 | Johnson et al. | |
| 4,970,152 A * | 11/1990 | Ashida et al. .................. | 435/19 |
| D325,090 S | 3/1992 | Karp et al. | |
| D330,428 S | 10/1992 | Lewis et al. | |
| 5,155,032 A | 10/1992 | Tanaka et al. | |
| 5,179,006 A | 1/1993 | Matuura et al. | |
| 5,266,461 A | 11/1993 | Tanaka | |
| D342,793 S | 12/1993 | Balmer | |
| D343,905 S | 2/1994 | Nagata et al. | |
| 5,286,625 A | 2/1994 | Tanaka et al. | |
| 5,310,657 A | 5/1994 | Berzofsky | |
| 5,316,911 A | 5/1994 | Baek et al. | |
| 5,318,893 A | 6/1994 | Matuura et al. | |
| D353,676 S | 12/1994 | Kelln et al. | |
| 5,372,946 A | 12/1994 | Cusak et al. | |
| 5,389,547 A | 2/1995 | Tanaka et al. | |
| 5,401,647 A | 3/1995 | Tanaka et al. | |
| 5,474,984 A | 12/1995 | Tanaka et al. | |
| 5,504,011 A | 4/1996 | Gavin et al. | |
| 5,518,006 A | 5/1996 | Mawhirt et al. | |
| 5,534,226 A | 7/1996 | Gavin et al. | |
| 5,550,030 A | 8/1996 | Tanaka et al. | |
| 5,574,023 A | 11/1996 | Shibata et al. | |
| 5,591,403 A | 1/1997 | Gavin et al. | |
| 5,591,628 A | 1/1997 | Baek et al. | |
| 5,605,806 A | 2/1997 | Tanaka et al. | |
| 5,637,474 A | 6/1997 | Takaoka et al. | |
| D380,555 S | 7/1997 | Kurosaki et al. | |
| 5,681,710 A | 10/1997 | Tanaka et al. | |
| 5,695,948 A | 12/1997 | Tanaka et al. | |
| 5,702,882 A | 12/1997 | Tamura et al. | |
| D390,661 S | 2/1998 | Foggia | |
| D391,373 S | 2/1998 | Shartle | |
| 5,731,212 A | 3/1998 | Gavin et al. | |
| 5,750,500 A | 5/1998 | Tsuchiya et al. | |
| 5,795,962 A | 8/1998 | Iwanaga et al. | |
| 5,800,781 A | 9/1998 | Gavin et al. | |
| 5,836,360 A | 11/1998 | Gavin et al. | |
| 6,046,021 A | 4/2000 | Bochner | |
| D437,419 S | 2/2001 | Kraack et al. | |
| D445,909 S | 7/2001 | Pogorzelski | |
| 6,270,982 B1 | 8/2001 | Jordan et al. | |
| 6,303,389 B1 | 10/2001 | Levin et al. | |

(Continued)

FOREIGN PATENT DOCUMENTS

EP 0121868 10/1984

(Continued)

OTHER PUBLICATIONS

Johansson et al. "Exocytosis of the prophenoloxidase activating system from crayfish hemocytes". Journal of Comparative Physiology B. 1985. vol. 156, pp. 175-181.*
Armstrong et al. "Endotoxin-induced degranulation of the Limulus amebocyte". Experimental Cell Research. 1982. vol. 140, pp. 15-24.*
Jiang et al. "Beta-1, 3-glucan recognition protein-2 betaGRP-2 from *Manduca sexta*: An acute-phase protein that binds beta-1, 3-glucan and lipoteichoic acid to aggregate fungi and bacteria and stimulate prophenoloxidase activation". Insect Biochemistry and Molecular Biology. (Jan. 2004), vol. 34, No. 1, pp. 89-100.*
Patent Coorporation Treaty (PCT) International Search Report ; International Application No. PCT/US2005/043426, completed Jul. 18, 2007 and mailed Aug. 9, 2007 (4 pages).

(Continued)

*Primary Examiner* — Vera Afremova
(74) *Attorney, Agent, or Firm* — Goodwin Procter LLP

(57) ABSTRACT

The invention provides methods and compositions for the detection and/or quantification of a Gram positive bacterial contaminant in a sample. In particular, the invention provides hemocyte-based preparations, methods of making such hemocyte-based preparations, and methods of using such hemocyte-based preparations for the detection and/or quantification of the Gram positive bacterial contaminant.

8 Claims, 11 Drawing Sheets

U.S. PATENT DOCUMENTS

| | | | |
|---|---|---|---|
| 6,306,659 | B1 | 10/2001 | Parce et al. |
| 6,391,570 | B1 | 5/2002 | Jordan et al. |
| 6,428,971 | B1 | 8/2002 | Shinabarger et al. |
| 6,440,722 | B1 | 8/2002 | Knapp et al. |
| D463,570 | S | 9/2002 | Bedingham et al. |
| 6,451,610 | B1 | 9/2002 | Gorman et al. |
| D472,324 | S | 3/2003 | Rumore et al. |
| 6,696,261 | B2 | 2/2004 | Patel et al. |
| 7,329,538 | B2 | 2/2008 | Wainwright et al. |
| 2003/0104501 | A1 | 6/2003 | Jordan et al. |
| 2004/0241788 | A1 | 12/2004 | Wainwright et al. |
| 2006/0216780 | A1 | 9/2006 | Wainwright et al. |
| 2008/0020422 | A1 | 1/2008 | Wainwright et al. |

FOREIGN PATENT DOCUMENTS

| | | |
|---|---|---|
| EP | 0816513 | 1/1998 |
| GB | A-2080524 | 2/1982 |
| JP | 61093958 | 5/1986 |
| WO | WO-83/02123 | 6/1983 |
| WO | WO-99/19355 | 4/1999 |
| WO | WO-99/53322 | 10/1999 |
| WO | WO-2005/010207 | 2/2005 |
| WO | WO-2006/076617 A2 | 7/2006 |
| WO | WO-2006/076617 A3 | 7/2006 |
| WO | WO-2007/078268 A2 | 7/2007 |

OTHER PUBLICATIONS

Aono et al., "Interaction Between Hemocytes and Plasma is Necessary for Hemolymph Coagulation in the Spiny Lobster, *Panulirus japonicus*," Comp. Biochem. Physiol. vol. 113A, No. 3, pp. 301-305 (1996).

Asokan et al., "Activiation pf Prophenoloxidase in the Plasma and Haemocytes of the Marine Mussel *Perna viridis* Linnaeus," Developmental and Comparative Immunology, vol. 21, No. 1, pp. 1-12 (1997).

Aspán et al., "cDNA Cloning of Prophenoloxidase from the Freshwater Crayfish *Pacifastacus leniusculus* and Its Activation," Proc. Nat'l Acad. Sci. USA, vol. 92, pp. 939-943 (Feb. 1995).

Aspán et al., "The Effect of Endogeneous Proteinase Inhibitors on the Prophenoloxidase Activating Enzyme, A Serine Proteinase from Crayfish Haemocytes," Insect Biochem, vol. 20, No. 5, pp. 485-492 (1990).

Bettencourt et al., "Hemolymph-Dependent and Independent Responses in *Drosophila* Immune Tissue," Journal of Cellular Biochemistry, 92:849-863 (2004).

Bullis, "Invertebrate Pathology: Responses to Injury and Disease," Aquavet II, Comparative Pathology of Aquatic Animals, Laboratory for Marine Animal Health, School of Veterinary Medicine, University of Pennsylvania, undated.

Burmester et al., "Origin and Evolution of Arthropod Hemocyanins and Related Proteins," J Comp Physiol B 172:95-107 (2002).

Charles River Laboratories, "In Vitro Pyrogen Test (IPT)," (2002).

Charles River Laboratories, "IPT Assay Steps," (2002).

"Comparative Immunology," Department of Comparative Physiology—Uppsala University, http://www.jamfys.ebc.uu.se/propo.html, printed May 22, 2002.

Cooper et al. "The Impact of Non-endotoxin LAL-Reactive Materials on *Limulus* Amebocyte Lysate Analysis," PDA Journal of Pharmaceutical Science & Technology, vol. 51.No. 1:2-6 (Jan.-Feb. 1997).

Datta et al., "Purification of a Unique glycoprotein that Enhances Phenol Oxidase Activity in Scorpion (*Heterometrus bengalensis*) Haemolymph," Biochem. J. vol. 260, 525-529 (1989).

Decker, et al., "SDS-Induced Phenoloxidase Activity of Hemocyanins from *Limulus polyphemus*, Eurypelma Californicum and Cancer Magister," The Journal of Biological Chemistry, vol. 276, No. 21, pp. 17796-17799 (May 2001).

Decker, et al., "Tarantula Hemocyanin Shows Phenoloxidase Activity," The Journal of Biological Chemistry, vol. 279, No. 40, pp. 25889-25892 (Oct. 1998).

De Kimpe et al., "The Cell Wall Components Peptidoglycan and Lipoteichoic Acid from *Staphylococcus aureus* Act in Synergy to Cause Shock and Multiple Organ Failure," Medical Sciences, pp. 10359-10363 (Oct. 1995).

Dunér, Kristina I., "A New Kinetic Single-Stage *Limulus* Amoebocyte Lysate Method for the Detection of Endotoxin in Water and Plasma," Journal of Biochemical and Biophysical Methods, vol. 26, pp. 131-142 (1993).

Gollas-Galván et al, "Prophenoloxidase from Brown Shrimp (*Penaeus californiensis*) Hemocytes," Comparative Biochemistry and Physiology Part B, 122: 77-82 (1999).

Ganguly et al., "Tyrosine Phosphorylation of a 94-kDa Protein of Human Fibroblasts Stimulated by Streptococcal Lipoteichoic Acid," The Journal of Biological Chemistry, vol. 260, No. 24, pp. 13342-13346 (Oct. 1985).

Geng et al., "Hemostatis in Larvae of *Manduca sexta*: Formation of a Fibrous Coagulum by Hemolymph Proteins," Biochemical and Biophysical Research Communications, vol. 155, No. 2, pp. 1060-1065 (Sep. 15, 1998).

Ginsburg, "Role of Lipoteichoic Acid in Infection and Inflammation," The Lancet Infectious Diseases, vol. 2, pp. 171-179 (Mar. 2002).

Goldsworthy et al., "Adipokinetic Hormone Enhances Laminarin and Bacterial Lipopolysaccharide-Induced Activation of the Prophenoloxidase Cascade in the African Migratory Locust," *Locusta migratoria*, Journal of Insect Physiology, 48:601-608 (2002).

Halwani et al., "Apolipophorin-III and the Interactions of Lipoteichoic Acids with the Immediate Immune Responses of *Galleria mellonella*," Journal of Invertebrate Pathology, 76, 233-241 (2000).

Hamada et al., "Chemical Properties and Immunobiological Activities of Streptococcal Lipoteichoic Acids," Zbl. Bakt. Hyg. A 259, 228-243 (1985).

Harrington et al., "Synthesis of Peptidoglycan and Teichoic Acid in *Bacillus subtilis*: Role of the Electrochemical Proton Gradient," Journal of Bacteriology, vol. 159, No. 3, pp. 925-933 (Sep. 1984).

Hauton et al., "Circatidal Rhythmicity in the Activity of the Phenoloxidase Enzyme in the Common Shore Crab, *Carcinus maenas*," Comp. Biochem. Physiol. vol. 111B, No. 3, pp. 347-352 (1995).

Hauton et al., "In Situ Variability in Phenoloxidase Activity in the Shore Crab, *Carcinus maenas* (L.)," Comp. Biochem. Physiol. vol. 117B, No. 2, pp. 267-271 (1997).

Hernandez-Lopez et al., "In the Spiny Lobster (*Panulirus interruptus*) the Prophenoloxidase is Located in Plasma not in Haemocytes," Fish & Shellfish Immunology, 14, 105-114 (2003).

Hurley, James C., "Endotoxeima: Methods of Detection and Clinical Correlates," Clinical Microbiology Reviews, vol. 8, No. 2, pp. 268-292 (Apr. 1995).

Iwanaga et al., "Chromogenic Substrates for Horseshoe Crab Clotting Enzyme: Its Application for the Assay of Bacterial Endotoxins," Hemostasis, Chapter 7, pp. 183-188 (1978).

Iwanaga Sadaaki, "The *Limulus* Clotting Reaction," Current Opinion in Immunology, Current Biology Ltd., vol. 5, No. 5, pp. 74-82 (1993).

Iwanaga, "The Molecular Basis of Innate Immunity in the Horseshoe Crab," Curr Opin Immunol, vol. 14, pp. 87-95 (2002).

Jiang et al., "Characterization and Functional Analysis of 12 Naturally Occurring Reactive Site Variants of Serpin-1 from *Manduca sexta*," The American Society for Biochemistry and Molecular Biology, Inc., vol. 272, No. 2, pp. 1082-1087 (Jan. 1997).

Jiang et al., "Pro-Phenol Oxidase Activating Proteinase from an Insect, *Manduca sexta*: A Bacteria-Inducible Protein Similar to *Drosophila easter*," Proc. Natl. Acad. Sci. USA, vol. 95, Issue 21, 12220-12225 (Oct. 1998), Biochemistry.

Jiang et al., "β-1, 3-Glucan Recognition Protein-2 (βGRP-2) from *Manduca sexta*: an Acute-phase Protein that Binds β-1, 3-Glucan and Lipoteichoic Acid to Aggregate Fungi and Bacteria and Stimulate Prophenoloxidase Activation," Insect Biochemistry and Molecular Biology, vol. 34, Issue 1, pp. 89-100 (2004).

Johansson et al., "Cellular Immunity in Crustaceans and the proPO System," Parasitology Today, vol. 5, No. 6, pp. 171-176 (1989).

Jolliffe et al., "The Energized Membrane and Cellular Autolysis in *Bacillus subtilis*," Cell, vol. 25, pp. 753-763 (Sep. 1981).

Kawabata et al., "The Clotting Cascade and Defense Molecules Found in the Hemolymph of the Horseshoe Crab," New Directions in Invertebrate Immunology, 255-283 (1996).

Kobayashi et al., "Detection of Peptidoglycan in Human Plasma Using the Silkworm Larvae Plasma Test," FEMS Immunology and Medical Microbiology, 28:49-53 (2000).

Lackie et al., "Invertebrate Immunity," Parasitology, 80:393-412 (1980).

Loker et al., "On Being a Parasite in an Invertebrate Host: A Short Survival Course," J. Parasitol., 80(5), p. 728-747 (1994).

Mattsson et al., "Highly Purified Lipoteichoic Acid from *Staphylococcus aureus* Induces Procoagulant Activity and Tissue Factor Expression in Human Monocytes by is a Weak Inducer in Whole Blood: Comparison with Peptidoglycan," Infection and Immunity, pp. 4322-4326 (Jul. 1004).

Morath et al., "Structural Decomposition and Heterogeneity of Commercial Lipoteichoic Acid Preparations," Infection and Immunity, pp. 938-944 (Feb. 2002).

Muta et al., "Limuls Factor C," Journal of Biological Chemistry, American Society of Biological Chemists-Baltimore, MD, vol. 266, No. 10, pp. 6554-6561 (1991).

Nagai et al., "A Link Between Blood Coagulation and Prophenol Oxidase Activation in Arthropod Host Defense," The Journal of Biological Chemistry, vol. 275, No. 38, pp. 29264-29267 (Sep. 2000).

Nagai et al., "Functional Conversion of Hemocyanin to Phenoloxidase by Horseshoe Crab Antimicrobial Peptides," The Journal of Biological Chemistry, vol. 276, No. 29, pp. 27166-27170 (Jul. 2001).

Nellaiappan et al., "On the Presence of Prophenoloxidase in the Hemolymph of the Horseshoe Crab, *Limulus*," Comp. Biochem. Physiol., vol. 113B, No. 1, pp. 163-168 (1996).

Obayashi et al., "A new chromogenic endotoxin-specific assay using recombined *Limulus* coagulation enzymes and its clinical applications," Clin. Chin. Acta 149:55-65 (1985).

Parrinello et al., "Phenoloxidases in Ascidian Hemocytes: Characterization of the Pro-Phenoloxidase Activating System," Comparative Biochemistry and Physiology Park B: Biochemistry and Molecular Biology, vol. 135, Issue 4, pp. 583-591 (2003).

Pearson et al, "Comparison of Chemical Analyses of Hollow-Fiber Dialyzer Extracts," Artificial Organs, vol. 8, No. 3:291-298 (1984).

Ratcliffe et al., "Activation of the Prophenoloxidase Cascade and Initiation of Nodule Formation in Locusts by Bacterial Lipopolysaccharides," Developmental and Comparative Immunology, vol. 15, pp. 33-39 (1991).

Roslansky et al., "Sensitivity of *Limulus* Amebocyte Lysate (LAL) to LAL-Reactive Glucans," J. of Clinical Microbiology, 29 (11):2477-2483 (1991).

Saul et al., "The Majority of Prophenoloxidase in the Hemolymph of *Manduca sexta* is Present in the Plasma and Not in the Hemocytes," Developmental and Comparative Immunology, vol. 11, pp. 479-485 (1987).

Seki et al., "Horseshoe Crab (1,3)-.beta.-D-Glucan-sensitive Coagulation Factor G," J. of Biological Chem. 269:1370-1374 (1994).

Shah et al., "A Novel Glucan-Binding Protein with Lipase Activity from the Oral Pathogen *Streptococcus mutans*," Microbiology, 150: 1947-1956 (2004).

Söderhäll, "Prophenoloxidase Activating System and Melanization—A Recognition Mechanism of Arthropods? A Review," Developmental and Comparative Immunology, vol. 6, pp. 601-611 (1982).

Söderhäll et al., "The Prophenoloxidase Activiating System and its Role in Invertebrate Defence," Annals of the New York Academy of Sciences, vol. 712, pp. 155-161 (Apr. 15, 1994).

Söderhäll et al., "Chapter 15 The Prophenoloxidase Activating System: The Biochemistry of its Activation and Role in Arthropod Cellular Immunity, with Special Reference to Crustaceans," Immunity in Invertebrates, pp. 208-223 (1986).

Sritunyalucksana et al., "Peroxinectin, a Cell Adhesive Protein Associated with the proPO System from the Black Tiger Shrimp, *Penaeus monodon*," Developmental and Comparative Immunology, 25: 353-363 (2001).

Sugumaran et al., "Lysolecithin—A Potent Activator of Prophenoloxidase from the Hemolymph of the Lobster, *Homarus americanus*," Biochemcial and Biophysical Research Communications, vol. 176, No. 3, pp. 1371-1376 (1991).

Tarsi-Tsuk et al., "Stimulation of the Resiratory Burst in Peripheral Blood Monocytes by Lipoteichoic Acid," The Journal of Immunology, vol. 144, No. 7, pp. 2665-2670 (Apr. 1990).

"The Horseshoe Crab," http://www.horseshoecrab.org/anat/anat.html, printed Aug. 6, 2002.

"The Prophenoloxidase (proPO) Activation System," http://sbs.umkc.edu/yux/PPO%20activation.html, printed Apr. 16, 2003.

Tsuchiya et al., "Detection of Peptidoglycan and β-Glucan with Silkworm Larvae Plasma Test," FEMS Immunology and Medical Microbiology, 15:129-134 (1996).

Tsuji et al., "Automation of Chromogenic Substrate *Limulus* Amebocyte Lystate Assay method of Endotoxin by Robotic System," Applied and Environmental Microbiology, vol. 48, No. 3, pp. 550-555 (Sep. 1984).

Vargas-Albores et al, "An Anticoagulant Solution for Haemolymph Collection and Prophenoloxidase Studies of Penaeid Shrimp (*Penaeus californiensis*)," Comp. Biochem. Physiol. vol. 106A, No. 2, pp. 299-303 (1993).

Wilson et al., "Identity of *Limulus* Amoebocyte Lysate-Active Root Surface Materials from Periodontally Involved Teeth," Journal of Clinical Periodontology, vol. 13, No. 8, pp. 743-747 (Sep. 1986).

Patent Cooperation Treaty (PCT) International Search Report; International Application No. PCT/US98/20823; mailed Mar. 3, 1999.

Patent Cooporation Treaty (PCT) IPER; International Application No. PCT/US98/20823, mailed Jan. 24, 2000.

Patent Cooperation Treaty (PCT) Invitation to Pay Additional Fees and Partial International Search; International Application No. PCT/US04/008013; mailed Dec. 10, 2004.

"The proPO-system," Department of Comparative Physiology, Uppsala University, available at http://www.jamfys.ebc.uu.se/propo.html, printed May 22, 2002.

Decker et al., "Recent Findings on Phenoloxidase Activity and Antimicrobial Activity of Hemocyanins," Developmental & Comparative Immunology, vol. 28, pp. 673-687 (2004).

Patent Cooperation Treaty (PCT) International Search Report; International Application No. PCT/US2004/008013, mailed on Apr. 8, 2005.

Patent Cooperation Treaty (PCT) Written Opinion of the International Searching Authority for PCT Application No. PCT/US2004/008013, mailed on Apr. 8, 2005.

Coates, D.A., "Enhancement of the Sensitivity of the *Limulus* Assay for the Detection of Gram Negative Bacteria," (1977) Journal of Applied Bacteriology 42: 445-449.

Inada et al., "A Silkworm Larvae Plasma Test for Detecting Peptidoglycan in Cerebrospinal Fluid is Useful for the Diagnosis of Bacterial Meningitis," (2003) Microbiology and Immunology, 47:(10): 701-707.

Janda et al., "A Colorimetric Estimation of Lipopolysaccharides," (1971) Febs Letters 16: (4): 343-345.

Maeda, M. et al., "Chromogenic Assay Method of Lipopolysaccharide (LPS) for Evaluating Bacterial Standing Crop in Seawater," (1979) Journal of Applied Bacteriology 47: 175-182.

Sigma Chemical Company E-Toxate Technical Bulletin (2000) No. 210: 1-4.

Wiegel, J. et al., "Determination of the Gram Type Using the Reaction Between Polymyxin B and Lipopolysaccarides of the Outer Cell Wall of Whole Bacteria," Journal of General Microbiology (1982) 128: 2261-2270.

Charles River Laboratories, "LAL Products and Services" (2001).

Prior, Richard B. Eds., (1990) "Chemical Applications of the *Limulus* Amebocyte Lysate Test" CRC Press, pp. 28-36.

Patent Cooperation Treaty (PCT) International Search Report; International Application No. PCT/US2006/001305, completed on Jul. 18, 2006.

Hausmann et al. (2000) "Gel Clot LAL Assay in the Initial Management of Peritoneal Dialysis Patients with Peritonitis: a Retrospective Study," Nephrology Dialysis Transplantation 15:680-683.

Mottar et al. (1993) "Routine *Limulus* Amoebocyte Lysate (LAL) Test for Endotoxin Determination of Milk Using a Toxinometer ET-201," Journal of Dairy Research 60:223-228.

Roth et al. (1989) "A Modified *Limulus* Amebocyte Lysate Test with Increased Sensitivity for Detection of Bacterial Endotoxin," J. Lab. Clin. Med. 114(3):306-311.

Morita et al. (1981) "A NEW (1→3)-β-D-Glucan-Mediated Coagulation Pathway Found In *Limulus* Amebocytes," FEBS Lett. 129:318-321.

Iwanaga et al. (1986) "The Hemolymph Coagulation System in Invertebrate Animals," J. Protein Chem. 5:255-268.

Levin et al. (1968) "Clottable Protein in *Limulus*: Its Localization and Kinetics of Its Coagulation by Endotoxin," Thromb. Diath. Haemorrh. 19:186-197.

Nakamura et al. (1986) "Lipopolysaccharide-Sensitive Serine-Protease Zymogen (factor C) Found in *Limulus* Hemocytes," Eur. J. Biochem. 154:511-521.

Muta et al. (1987) "Primary Structure of Anti-Lipopolysaccharide Factor from American Horseshoe Crab, *Limulus polyphemus*," J. Biochem. 101:1321-1330.

Ho et al., (1993) "Electrophoretic Analysis of Endotoxin-Activated Gelation Reaction of *Carcinoscorpius rotundicauda* Amoebocyte Lysate," Biochem. & Mol. Biol. Int. 29:687-694.

Iwanaga (2007) "Biochemical Principle of *Limulus* test for Detecting Bacterial Endotoxins," Proc. Jpn. Acad., 83:110-119.

Pearson et al. (1980) "The Significance of *Limulus* Amebocyte Lysate Test Specificity on the Pyrogen Evaluation of Parenteral Drugs," Journal of Parenteral Drug Association 34(2):103-108.

Soderhall et al. (1985) "The Effects of β1,3-Glucans on Blood Coagulation and Amebocyte Release in the Horseshoe Crab, *Limulus polyphemus*," Bio. Bull. 169:661-674.

Vasse et al. (1999) "Prophenoloxidase Is Not Activated by Microbial Signals in *Limulus polyphemus*," Biol. Bull. 197:281-282.

Wildfeurer et al. (1974) "Investigations on the Specificity of the *Limulus* test for the Detection of Endotoxin," Applied Microbiology 28(5):867-871.

* cited by examiner

Prophenoloxidase Activation in *Cancer borealis*

Lipoteichoic Acid (LTA)

⇩

LTA Binding Protein

⇩

Serine Protease Cascade

⇩

Prophenoloxidase　　　Prophenoloxidase
Activating Enzyme　　　Activating Enzyme
Precursor

⇩

Prophenoloxidase　　　Phenoloxidase

⇩ substrate

Figure 2

METHODS FOR THE DETECTION AND/OR QUANTIFICATION OF GRAM POSITIVE BACTERIAL CONTAMINANTS

RELATED APPLICATIONS

This application claims the benefit of and priority to U.S. Patent Application Ser. No. 60/632,785, filed Dec. 2, 2004, the entirety of which is incorporated herein by reference.

GOVERNMENT SUPPORT

This invention was made in part with government support under grant number NAG 2-1263 from the National Aeronautics and Space Administration. The United States Government has certain rights in this invention.

FIELD OF THE INVENTION

The present invention relates generally to methods and compositions for detecting and/or quantifying Gram positive bacteria in a sample. More particularly, the invention relates to a hemocyte-based preparation useful in detecting and/or quantifying Gram positive bacteria in a sample, and to methods of making and using such a preparation.

BACKGROUND OF THE INVENTION

Microbial contamination by, for example, Gram positive bacteria, Gram negative bacteria, yeast, fungi, and molds may cause severe illness and, in some cases, even death in humans. Manufacturers in certain industries, for example, the pharmaceutical, medical device, water, and food industries, must meet exacting standards to verify that their products do not contain levels of microbial contaminants that would otherwise compromise the health of the recipient. These industries require frequent, accurate, and sensitive testing for the presence of such microbial contaminants to meet certain standards, for example, standards imposed by the United States Food and Drug Administration (USFDA) or the Environmental Protection Agency. By way of example, the USFDA requires certain manufacturers of pharmaceuticals and invasive medical devices to establish that their products are free of detectable levels of Gram negative bacterial endotoxin.

To date, a variety of assays have been developed to detect the presence and/or amount of a microbial contaminants in a test sample. One family of assays use hemocyte lysates prepared from the hemolymph of crustaceans, for example, horseshoe crabs. These assays typically exploit, in one way or another, a clotting cascade that occurs when the hemocyte lysate is exposed to a microbial contaminant. For example, FIG. 1 shows a schematic representation of certain clotting cascades known to be present in hemocyte lysate produced from the hemolymph of the horseshoe crab, *Limulus polyphemus*. Such lysates are known in the art as *Limulus amebocyte* lysate or LAL.

As shown in FIG. 1, the coagulation system of LAL, like the mammalian blood coagulation system, comprises at least two coagulation cascades that include an endotoxin or lipopolysaccharide (LPS) mediated pathway (the Factor C pathway) and a $(1\rightarrow 3)$-$\beta$-D glucan mediated pathway (the Factor G pathway). See, for example, Morita et al. (1981) FEBS LETT. 129: 318-321; and Iwanaga et al. (1986) J. PROTEIN CHEM. 5: 255-268.

It is understood that Gram negative bacteria can be detected using LAL based assays. For example, Gram negative bacteria produce endotoxin or LPS, which after binding to LPS binding protein activates the Factor C pathway in LAL (see, FIG. 1). The endotoxin or LPS-mediated activation of LAL is well understood and has been thoroughly documented in the art. See, for example, Levin et al. (1968) THROMB. DIATH. HAEMORRH. 19: 186; Nakamura et al. (1986) EUR. J. BIOCHEM. 154: 511; Muta et al. (1987) J. BIOCHEM. 101: 1321; and Ho et al. (1993) BIOCHEM. & MOL. BIOL. INT. 29: 687. When bacterial endotoxin is contacted with LAL, the endotoxin initiates a series of enzymatic reactions, known as the Factor C pathway, that are understood to involve three serine protease zymogens called Factor C, Factor B, and pro-clotting enzyme (see, FIG. 1). Briefly, upon exposure to endotoxin, the endotoxin-sensitive factor, Factor C, is activated. Activated Factor C thereafter hydrolyses and activates Factor B, whereupon activated Factor B activates proclotting enzyme to produce clotting enzyme. The clotting enzyme thereafter hydrolyzes specific sites, for example, $Arg^{18}$-$Thr^{19}$ and $Arg^{46}$-$Gly^{47}$ of coagulogen, an invertebrate, fibrinogen-like clottable protein, to produce a coagulin gel. See, for example, U.S. Pat. No. 5,605,806.

Furthermore, it is also understood that $(1\rightarrow 3)$-$\beta$-D glucans and other LAL-reactive glucans, produced by microorganisms such as yeasts and molds, can also activate the clotting cascade of LAL, through a different enzymatic pathway known as the Factor G pathway (see, FIG. 1). It is understood that Factor G is a serine protease zymogen that becomes activated by $(1\rightarrow 3)$-$\beta$-D glucan or other LAL reactive glucans. Upon exposure to $(1\rightarrow 3)$-$\beta$-D glucan, for example, Factor G is activated to produce activated Factor G. It is understood that activated Factor G thereafter converts the proclotting enzyme into clotting enzyme, whereupon the clotting enzyme converts coagulogen into coagulin.

Presently, LAL is employed as the amebocyte lysate of choice in many assays for detecting the presence of Gram negative bacteria, fungus or molds because of its sensitivity, specificity, and relative ease for avoiding interference by other components that may be present in a sample. For example, LAL, when combined with a sample containing bacterial endotoxin and optionally with certain LAL substrates, reacts with the endotoxin in the sample to produce a detectable product, such as a gel, increase in turbidity, or a colored or light-emitting product in the case of a synthetic chromogenic substrate. The resulting product may be detected, for example, either visually or by the use of an optical detector.

In contrast, assays of comparable sensitivity and specificity for detecting and/or quantifying Gram positive bacterial contaminants have been more difficult to develop. One assay for detecting Gram positive bacterial contamination, known as the In Vitro Pyrogen Test (IPT), is available from Charles River Laboratories (Wilmington, Mass.). The IPT assay is an in vitro alternative to the rabbit pyrogen test, and is an ELISA-based assay that uses fresh or cryopreserved human whole blood. When exposed to pyrogens, immune cells within the whole blood produce interleukin-1$\beta$ that is detected in the ELISA assay. The IPT assay, however, does not selectively detect the presence of Gram positive bacteria, as it is activated by pyrogens present in Gram positive bacteria, Gram negative bacteria, yeasts and viruses.

Although the detection of bacterial, yeast and fungal contamination can be extremely important, the ability to discriminate between these different organisms can provide useful information about an infectious agent causing an infection in an individual or the source and type of contamination present in a test sample. For example, once an infectious agent has been identified, a physician can then prescribe the most appropriate medication for treating an infection. Furthermore, once the type of bacterial, yeast or fungal contamination has been identified, then this type of information may speed up the process of identifying the source of contamination in, for example, a water supply. As a result, once the source of contamination has been identified, further contamination can be mitigated. Although methods and compositions currently are available for specifically detecting Gram negative bacteria, yeasts, and molds, there is still an ongoing need for further methods and compositions for specifically detecting Gram positive bacteria in a sample of interest.

SUMMARY OF THE INVENTION

The invention generally provides methods and compositions useful in detecting the presence and/or amount of lipoteichoic acid, a molecule found within the cell wall of Gram positive bacteria. This information can be used to determine whether Gram positive bacteria are present in a test sample and also can be used to measure the extent of contamination in a test sample.

In one aspect, the invention provides a method of producing a preparation for detecting the presence and/or amount of lipoteichoic acid in a sample. The invention comprises the steps of: (a) providing a hemocyte preparation harvested from a crustacean selected from a group consisting of *Cancer borealis, Cancer irroratus, Hemigrapsus sanguineus*, and *Limulus polyphemus*, wherein the hemocytes contain lipoteichoic acid reactive material; (b) releasing the lipoteichoic acid reactive material from the hemocytes; and (c) harvesting the lipoteichoic acid reactive material released from the hemocytes.

In step (b), the lipoteichoic acid can be released from the hemocytes by a variety of procedures. For example, the hemocytes may be lysed by conventional procedures, for example, by osmotic shock, sonication, homogenization, and ultracentrifugation. Alternatively, the outer membrane of the hemocytes may be rendered permeable, for example, selectively permeable, to the lipoteichoic acid reactive material disposed within the hemocytes. In this approach, the hemocytes can be rendered permeable to lipoteichoic acid reactive material by exposing the hemocytes to a membrane permeabilizing agent. Although a variety of membrane permeabilizing agents can be used, a preferred membrane permeabilizing agent is an ionophore, for example, a calcium ionophore. The ionophore is admixed with the preparation to give a final concentration in the range from about 0.1 µM to about 100 µM, for example, from about 1 µM to about 10 µM. When a calcium ionophore is used, the ionophore preferably is combined with divalent cations, for example, calcium ions.

The resulting preparation of lipoteichoic acid reactive material comprises the pro-enzyme pro-phenol oxidase. Furthermore, the preparation, when made, contains lipoteichoic acid reactive material that is substantially inactive at the time the preparation is made. However, when the preparation is later combined with lipoteichoic acid, the lipoteichoic acid reactive material becomes activated whereupon the pro-phenol oxidase is converted into phenol oxidase. In order to assay the amount of phenol oxidase in a test sample, the preparation can be combined with one or more substrates for phenol oxidase. The phenol oxidase then acts on or converts the substrate into a product that can be detected and/or quantified either by visual inspection or by means of a detector, for example, an optical detector, such as, a spectrophotometer, fluorimeter, or the like.

In another aspect, the invention provides preparations of lipoteichoic acid reactive material that can be produced by the foregoing methods. The preparations comprise the pro-enzyme pro-phenol oxidase. When produced, the lipoteichoic acid reactive material contained within the preparation is substantially inactive. However, when exposed to lipoteichoic acid, for example, lipoteichoic acid present in and on Gram positive bacteria, the lipoteichoic acid reactive material becomes activated and the pro-phenol oxidase is converted into phenol oxidase. The active phenol oxidase enzyme can then act on or convert a substrate to produce a detectable product (either visually detectable or by means of a detector).

The invention provides a composition comprising an isolated enzyme preparation derived from crustacean hemocytes. The preparation comprises pro-phenol oxidase, which becomes converted into phenol oxidase when the enzyme preparation is contacted with lipoteichoic acid, for example, lipoteichoic acid present in or on Gram positive bacteria. It is understood that this type of preparation can be produced by rendering the outer membranes of crustacean hemocytes permeable, for example, selectively permeable, to pro-phenol oxidase as well as other components of the crustacean's pro-phenol oxidase cascade. Such a preparation can be produced from the hemocytes derived from crustaceans selected from the group consisting of crustaceans selected from the group consisting of *Cancer borealis, Cancer irroratus, Carcinus maenas, Hemigrapsus sanguineus*, and *Limulus polyphemus*.

The invention also provides a crustacean hemocyte lysate comprising pro-phenol oxidase, which is converted into phenol oxidase when the hemocyte lysate, after preparation, is subsequently contacted with lipoteichoic acid, for example, lipoteichoic acid present in or on Gram positive bacteria. The crustacean hemocytes can be derived from a crustacean selected from the group consisting of *Cancer borealis, Cancer irroratus, Carcinus maenus, Hemigrapsus sanguineas*, and *Limulus polyphemus*.

The foregoing preparations can be combined with a substrate for phenol oxidase. Accordingly, when the preparation is activated by exposure to lipoteichoic acid reactive material from Gram positive bacteria, the substrate is converted into a product that can be detected and/or quantified by visual inspection or by means of a detector, for example, an optical detector.

Depending upon the choice of the starting materials and the preparation conditions, it is possible to produce an isolated enzyme preparation substantially free of Factor C activity and/or Factor G activity. The resulting preparation can remain substantially inactive in the presence of (i) one of $(1\rightarrow 3)$-β-D glucan, lipopolysaccharide or proteoglycan, (ii) a combination of $(1\rightarrow 3)$-β-D glucan and lipopolysaccharide, a combination of $(1\rightarrow 3)$-β-D glucan and proteoglycan, or a combination of lipopolysaccharide and proteoglycan, or (iii) a combination of $(1\rightarrow 3)$-β-D glucan, lipopolysaccharide and proteoglycan. For example, an enzyme preparation can be produced by permeabilization of the hemocyte membranes of the crustacean Cancer borealis. For example, when hemocytes of the crustacean, *Cancer borealis*, are rendered permeable to lipoteichoic acid reactive material by exposure to a membrane permeabilizing amount of an ionophore, for example, a calcium ionophore, the resulting preparation containing lipoteichoic reactive material is substantially free of the Factor C cascade and of the Factor G cascade. As a result, this preparation is activated by, and thus detects the presence of, Gram positive bacteria but not Gram negative bacteria or yeast and fungus.

In contrast, when hemocytes of the crustacean *Limulus polyphemus* are lysed by conventional procedures, for example, by osmotic shock, sonication, homogenization, and ultracentrifugation, or rendered permeable, for example, using a membrane permeabilizing amount of an ionophore, the resulting preparation containing lipoteichoic acid reactive material also contains a complete Factor C cascade and a Factor G cascade. As a result, the resulting lysate is activated by, and thus detects the presence of, Gram positive bacteria, Gram negative bacteria, and yeast and fungus.

In another aspect, the invention provides methods of detecting the presence and/or amount of Gram positive bacteria in a test sample. The method comprises contacting the sample to be tested with one or more of the foregoing preparations. It is contemplated that the lysates may be used in a variety of different assays, for example, endpoint chromogenic assays, single-step kinetic assays, and multi-step kinetic assays. Furthermore, it is contemplated that the assays can be run in a variety of different formats, for example, in a well, a microtitre plate, or in an optical cartridge. The assays can be used to detect the presence and/or quantity of Gram positive bacteria in a liquid sample of interest. In addition, solid samples can be analyzed after contact or solubilization in a liquid sample. Furthermore, swabs of a solid surface can be analyzed after the swab has been contacted or solubilized in a liquid sample.

These aspects and features of the invention may be more completely understood by reference to the drawings, detailed description, and claims that follow.

BRIEF DESCRIPTION OF THE DRAWINGS

The invention may be more clearly understood by reference to the drawings, wherein:

FIG. 2 is a schematic representation showing the pro-phenol oxidase activation cascades in *Cancer borealis* hemocytes;

FIGS. 5A-5D are schematic illustrations of an exemplary cartridge in which FIG. 5A is a view of a bottom half of an exemplary cartridge showing the locations of immobilized hemocyte preparation and pro-phenol oxidase substrate, FIG. 5B is a view of a top half of an exemplary cartridge of the invention, FIG. 5C is a cross-sectional view of the fabricated cartridge through section A-A, and FIG. 5D is a cross-sectional view of the fabricated cartridge through section B-B;

DETAILED DESCRIPTION

The invention is based, in part, upon the discovery that it is possible to produce a hemocyte-based preparation that reacts with the lipoteichoic acid present in or on Gram positive bacteria. As a result, the hemocyte preparations of the invention can be used to detect and/or quantitate the presence of Gram positive bacteria in a test sample.

The hemocyte preparations of the invention contain lipoteichoic acid reactive material. Depending upon the source of the starting material and the hemocyte treatment conditions, it is possible to produce a preparation that reacts specifically with lipoteichoic acid. This preparation can detect the presence and/or amount of Gram positive bacteria in a sample of interest. Alternatively, using a different starting material and different hemocyte treatment conditions, it is possible to produce a preparation that reacts with lipoteichoic acid, proteoglycan, lipopolysaccharide and $(1\rightarrow 3)$-$\beta$-D glycan. Accordingly, this preparation can detect the presence and/or amount of Gram positive bacteria, Gram negative bacteria, and yeast and molds in a sample of interest.

FIG. 2 shows the clotting cascades present in hemocytes derived from *Cancer borealis*. According to FIG. 2, lipoteichoic acid (LTA), when present, binds to a LTA binding protein. Without wishing to be bound by theory, it is understood that the LTA binding protein then activates a serine protease cascade, which in turn converts a pro-phenol oxidase activating enzyme precursor into active pro-phenol oxidase activating enzyme. The pro-phenol oxidase activating enzyme, when activated, converts pro-phenol oxidase into phenol oxidase. Activated phenol oxidase then reacts with a phenol oxidase substrate, for example, isoprenaline sulfate, to produce a product, for example, a colored product.

Figure 1:
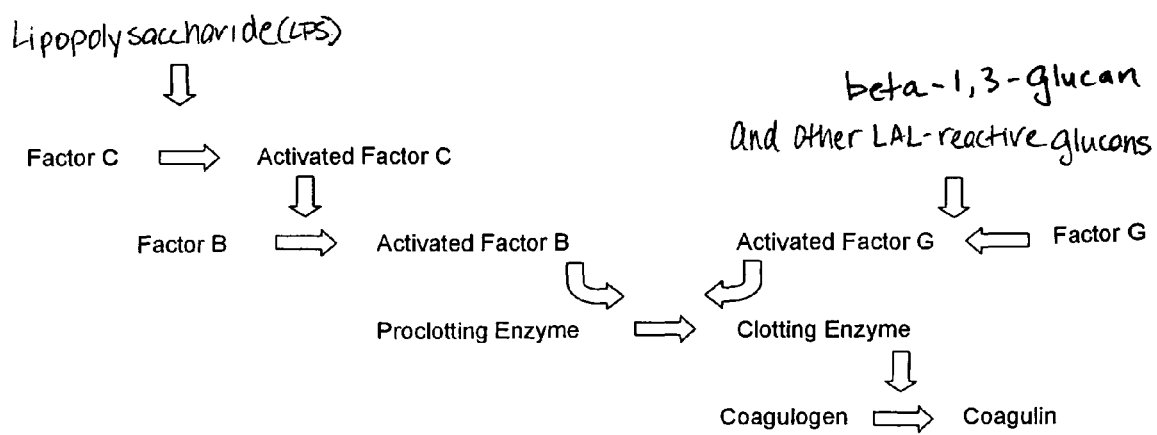
FIG. 1 is a schematic representation of the Factor C and Factor G cascades present in *Limulus amebocyte* lysate.
Figure 3:
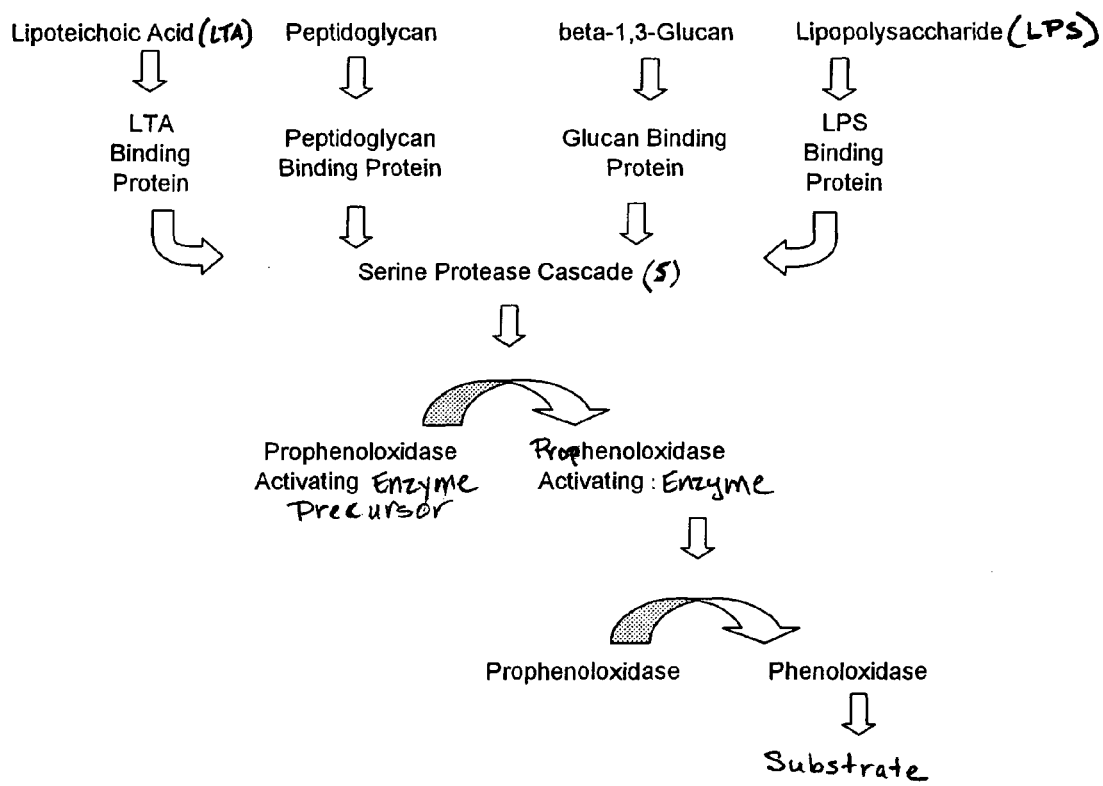
FIG. 3 is a schematic representation showing the pro-phenol oxidase activation cascade present in *Limulus polyphemus* hemocytes.

FIG. 3 shows the clotting cascades present in hemocytes derived from *Limulus polyphemus*. *Limulus* hemocytes are understood to be reactive with lipoteichoic acid, peptidoglycan, $(1\rightarrow 3)$-$\beta$-D glucan, and lipopolysaccharide, which, by a variety of mechanisms, can produce phenol oxidase, which can then react with a phenol oxidase substrate, for example, isoprenaline sulfate, to produce a colored product. Without wishing to be bound by theory, it is understood that LTA is bound by a LTA binding protein, proteoglycan is bound by a proteoglycan binding protein, $(1\rightarrow 3)$-$\beta$-D glucan is bound by a $(1\rightarrow 3)$-$\beta$-D glucan binding protein, and lipopolysaccharide is bound by a lipopolysaccharide binding protein. The binding proteins, once bound to their particular ligands, activate one or more serine protease cascades. The serine protease cascade(s) then converts a pro-phenol oxidase activating enzyme precursor into a phenol oxidase activating enzyme. The phenol oxidase activating enzyme then converts pro-phenol oxidase into phenol oxidase, which then reacts with a phenol oxidase substrate isoprenaline sulfate to produce a product, for example, a colored product.

Accordingly, depending upon the starting material and the extraction procedure, it is possible to produce a hemocyte preparation that is activated (i) only by lipoteichoic acid or (ii) by lipoteichoic acid as well as lipopolysaccharide and $(1\rightarrow 3)$-

β-D glucan. For example, hemocytes may be harvested from *Cancer borealis*, which once harvested can either be permeablized or lysed to release the lipoteichoic acid reactive material disposed therein.

The term "lipoteichoic acid reactive material" is understood to mean an isolated preparation derived from hemocytes, which, when contacted with lipoteichoic acid is capable of converting pro-phenol oxidase into phenol oxidase.

The source of hemocytes, extraction procedures, assays and assay formats useful in the practice of the invention will now be discussed in more detail below.

Hemocyte Preparation

As discussed, the hemocytes can be harvested from a variety of different crustaceans selected from crabs belonging to the *Cancer* genus, for example, *Cancer borealis, Cancer irratus, Carcinus maenas, Hemigrapsus sanguineus* (Japanese Shore Crab), crabs belonging to the *Limulus* genus, for example, *Limulus polyphemus*, crabs belonging to the *Tachypleus* genus, for example, *Tachypleus gigas*, for example, *Tachypleus tridentatus*, and crabs belonging to the *Carcinoscorpius* genus, for example, *Carcinoscorpius rotundicauda*.

Once harvested, the hemocytes can be lysed using conventional techniques known in the art, for example, by osmotic shock, homogenization, ultrasonication and ultracentrifugation. For example, crude lysates may be produced using the procedure as originally described in Levin et al. (1968) THROMB. DIATH. HAEMORRH. 19: 186, with modification, or in Prior (1990) "Clinical Applications of the *Limulus Amebocyte* Lysate Test" CRC Press 28-36 and 159-166, and in U.S. Pat. No. 4,322,217.

Alternatively, the outer membranes of the hemocyte can be rendered permeable to lipoteichoic acid reactive material disposed therein. This can be accomplished using a variety of membrane permeabilizing agents known in the art, for example, salt solutions, detergents, antibiotics, and ionophores.

Exemplary salt solutions include, for example, sodium chloride, potassium chloride, sodium acetate, magnesium chloride, magnesium sulfate, calcium chloride, calcium sulfate, and combinations of salts, such as those found in seawater. Exemplary detergents include, for example, Triton X-100, Tween-20, Nonidet P-40 and other non-ionic detergents. Exemplary antibiotics include, for example, gramicidin, polymyxin, and tetracycline. Exemplary ionophores include, for example, calcium ionophores, for example, calcium ionophore A23187, also known as C-7522, available from Sigma Chemical Co., St. Louis, Mo., calcium ionophore II 21193 from Fluka, Switzerland, and calcium ionophore IV 21198 from Fluka, Switzerland.

The calcium ionophores preferably are admixed with the hemocyte preparation to give a final concentration in the range from about 0.1 μM to about 100 μM, preferably in the range from about 1 μM to about 10 μM. In order to improve the activity of the calcium ionophore, the ionophore can be combined with divalent cations, for example, calcium chloride in the range from about 0.1 mM to about 100 mM, preferably in the range from about 1 mM to about 10 mM.

For example, the hemocytes, when harvested, are washed in a salt solution containing, for example, 0.45 M sodium chloride, 0.1 M glucose, 0.1 M cacodylic acid pH 7.0+/−1.0 pH units. The washed hemocytes then are combined with a release solution containing a ionophore to release the lipoteichoic acid reactive material from the hemocytes. An exemplary release solution contains, for example, 0.45 M sodium chloride, 0.1 M glucose, 0.1 M cacodylic acid, 3 μM calcium ionophore, 5 μM calcium chloride pH 7.0+/−1.0 pH units.

The lipoteichoic acid reactive material, once released from the hemocytes, can be used immediately or stored for later use. For example, the hemocyte preparation may be lyophilized under standard conditions, or frozen and stored at a temperature from −20° C. to −80° C. until use.

The resulting hemocyte preparations contain lipoteichoic acid reactive material, which when activated converts pro-phenol oxidase into phenol oxidase. The preparations can also be combined with a phenol oxidase substrate including, for example, isoprenaline sulfate (I0261, TCI-GR, Tokyo, Japan), isoproternol hemisulfate salt (I-5752, Sigma Chemical Co., St. Louis, Mo.), catechol (C-9510, Sigma Chemical Co., St. Louis, Mo.), 4-methylcatechol (M3,420-0 Aldrich Chemical Company Inc., Milwaukee, Wis.), L-dopa (D-9628, Sigma Chemical Co., St. Louis, Mo.), dopamine (H-8502, Sigma Chemical Co., St. Louis, Mo.), and 2',7'-dichlorodihydrofluorescein diacetate (D-399, Molecular probes, Eugene, Oreg.).

Depending upon the source of the starting material, for example, hemocytes harvested from the crustaceans *Cancer borealis*, it is possible to produce a preparation that is substantially free of Factor C activity and/or factor G activity. In other words, these preparations are not activated by lipopolysaccharide and/or (1→3)β-D glucan, respectively. Similarly, it is possible to produce hemocyte preparations that are not activated by proteoglycan.

In addition, it is possible to reconstitute a hemocyte preparation having a desired specificity for lipoteichoic acid, (1→3) β-D glucan, and lipopolysaccharide. For example, a lipoteichoic acid specific hemocyte preparation harvested from *Cancer borealis*, can be combined with a Factor C specific hemocyte preparation known in the art or a Factor G specific hemocyte preparation known in the art. As such it is possible to create a hemocyte preparation that is reactive with lipoteichoic acid and either (1→3)β-D glucan or lipopolysaccharide. Alternatively, it is possible to create a hemocyte preparation that is reactive with lipoteichoic acid, (1→3)β-D glucan and lipopolysaccharide by combining a lipoteichoic acid specific hemocyte preparation harvested from *Cancer borealis* with crude *Limulus amebocyte* lysate containing both the Factor C and Factor G cascades. The resulting hemocyte preparation, therefore, is reactive with lipoteichoic acid, (1→3)-β-D glucan and lipopolysaccharide.

In addition, it is understood that under certain circumstances, it is possible to create a crude *Limulus amebocyte* lysate that is reactive with lipoteichoic acid, (1→3)-β-D glucan, lipopolysaccharide and proteoglycan. It appears that crude *Limulus amebocyte* lysate contains an inhibitor that reduces lipoteichoic acid reactivity. However, the preparation can be diluted to dilute the concentration of the inhibitor present in the hemocyte preparation. Accordingly, by choosing the appropriate dilution, it is possible to produce a crude *Limulus amebocyte* lysate that is reactive with lipoteichoic acid (present in or on Gram positive bacteria), lipopolysaccharide (present in or on Gram negative bacteria), (1→3)-β-D glucan (present in or on fungus and molds) and, optionally, proteoglycan (present in or on Gram positive bacteria).

As will be apparent to one of ordinary skill, any buffer and salt known to promote activation of phenol oxidase in hemocyte preparations, as well as buffers to avoid extremes of pH that could inactivate the cascade, preferably are included in the hemocyte preparation. Although any of the buffers and salts that are understood in the art to be compatible with the hemocyte preparation may be used, buffer solutions comprising, for example, cacodylic acid, citrate, phosphate, PIPES, MOPS, HEPES, and Tris(tris(hydroxy)aminomethane). Typical formulation additives may include, without limitation, about 100-300 mM NaCl, about 10-100 mM divalent cations (e.g., $Mg^{2+}$ or $Ca^{2+}$), biocompatible buffers, e.g., Tris(tris(hydroxy)aminomethane), to give a final pH of about 6.5 to about 8.5, and, if the lysate is to be freeze dried, then sugars, e.g., mannitol or dextran and viscosity increasing agents such as polyvinyl alcohol (or anti-frothing agents including polyvinyl alcohol and polypropylene glycol).

Exemplary Assays

Assays specific for detecting the presence of Gram positive bacteria in a test sample can be prepared with the hemocyte-based preparations of the invention. Although various types of assays can be performed with the preparation, as discussed below, each of the assays of the invention generally involve contacting the preparation with a test sample in the presence of a phenol oxidase substrate. Phenol oxidase substrates include, for example, isoprenaline sulfate (I0261, TCI-GR, Tokyo, Japan), isoproternol hemisulfate salt (I-5752, Sigma Chemical Co., St. Louis, Mo.), catechol (C-9510, Sigma Chemical Co., St. Louis, Mo.), 4-methylcatechol (M3,420-0 Aldrich Chemical Company Inc., Milwaukee, Wis.), L-dopa (D-9628, Sigma Chemical Co., St. Louis, Mo.), dopamine (H-8502, Sigma Chemical Co., St. Louis, Mo.), and 2',7'-dichlorodihydrofluorescein diacetate (D-399, Molecular probes, Eugene, Oreg.).

Inhibition or enhancement of the assay occurs when substances in the test sample interfere with the hemocyte preparation reaction. Inhibition results in a longer reaction time, indicating lower levels of microbial contamination than may actually be present in the test sample. Enhancement results in shorter reaction time, indicating higher levels of microbial contamination than may actually be present in the test sample. To verify the lack of inhibition or enhancement, an aliquot of test sample (or a dilution of the test sample) is "spiked" with a known amount of an agent representative of the microbial contaminant to be measured, for example, lipoteichoic acid. It is recommended that the microbial contaminant spike results in a final microbial contaminant concentration in the sample equal to the mid-point, on a log basis, between the microbial contaminant concentration of the highest and lowest standards in the standard curve. For example, in an assay with a standard curve spanning from 50 PPO Units/mL to 0.005 PPO Units/mL, samples should be spiked to contain a final microbial contaminant concentration of 0.5 PPO Units/mL. In an assay with a standard curve spanning from 1 PPO Units/mL to 0.01 PPO Units/mL, the microbial contaminant spike should result in a final microbial contaminant concentration of 0.1 PPO Units/mL.

The spiked sample is assayed in parallel with the unspiked sample. The resulting microbial contaminant concentration in the unspiked sample and the microbial contaminant recovered in the spiked sample then are calculated. The microbial contaminant recovered should equal the known concentration of the spike within about 25%. If the test sample (or dilution) is found to inhibit or enhance the reaction, the sample may require further dilution until the inhibition or enhancement is overcome. Initially, one may want to screen for inhibition or enhancement by testing 10-fold dilutions of test sample. Once the approximate non-inhibitory or non-enhancing dilution is determined, the exact dilution can be found by testing two-fold dilutions around this dilution. The degree of inhibition or enhancement will be dependent upon the concentration of the test sample. If several concentrations of the same sample are to be assayed, it is necessary to establish performance characteristics for each concentration independently.

Gram positive bacteria can be detected using the preparations of the invention in a variety of different assays. For example, end point chromogenic assays, single-step kinetic assays, and/or multi-step kinetic assays can be performed in optical cuvettes, microtiter plates and the like. A variety of different assays and assay formats are described, for example, in published U.S. patent application 2004-0241788. By way of example, cartridge-based assays are described in more detail below.

The Cartridge

Exemplary cartridges useful in the practice of the invention are shown schematically in FIGS. 4A-4D. In general, the cartridge is an optical cartridge containing an immobilized hemocyte preparation for use in hemocyte preparation-based assays. These cartridges may be used alone or together with an optical detector, for example, a hand held optical detector. Although methods of the invention can be practiced without use of the cartridge, methods of the invention are particularly effective when combined the cartridge to provide a system that can be used in the field to provide rapid test results. This facilitates quicker elimination and/or treatment of microbial contamination.

A number of assays for the detection and/or quantification of a microbial contaminant can be performed in the cartridge of the invention, for example, as illustrated in FIG. 4. The cartridge may be used on its own and the test result detected by eye or it may be used in combination with an optical detector, for example, a hand-held optical detector as shown and described in U.S. Pat. No. Des. 390,661.

By way of example and as illustrated in FIGS. 4A-4D, cartridge 1 has a substantially planar housing fabricated, for example, from a moldable biocompatible material. The housing may be fabricated from any material, however, transparent and/or translucent glass or polymers are preferred. Preferred polymers include, for example, polystyrene, polycarbonate, acrylic, polyester, optical grade polymers, or any plastic such that the optical cell is substantially transparent. The housing contains at least one fluid inlet port 4, at least one optical cell 6, and at least one conduit 8 having a fluid contacting surface for providing fluid flow communication between the fluid inlet port 4 and optical cell 6. The only requirements for the optical cell 6 are that it defines a void capable of containing a sample to be tested and that a portion of the optical cell 6 is transparent to light. Cartridge 1 may also have at least one pump port 12 in fluid flow communication with fluid inlet port 4 and optical cell 6 for attaching the cartridge 1 to a pump. The pump may then impart a negative pressure via pump port 12 to pull the sample from fluid inlet port 4 to optical cell 6. A hemocyte preparation is disposed on a first region 14 of the fluid contacting surface of conduit 8, so that when a sample is applied to fluid inlet port 4, the sample traverses region 14 and solubilizes or reconstitutes the hemocyte preparation into the sample as it moves toward optical cell 6. This type of cartridge 1 may be used for determining whether a detectable change has occurred in the sample. In one embodiment, a phenol oxidase substrate is applied to the surface of the conduit 8 at first region 14 together with the hemocyte preparation. This type of cartridge 1 may be used for performing, for example, a kinetic chromogenic assay.

In another embodiment, as illustrated in FIGS. 4A-4D, a second region 16 of the fluid contacting surface of conduit 8 is spaced apart from and downstream of first region 14. In this configuration, a hemocyte preparation is disposed at first region 14 and a phenol oxidase substrate is disposed at second region 16, so that after the sample is contacted with the hemocyte preparation in region 14, the sample-hemocyte preparation mixture traverses conduit 8 and contacts the phenol oxidase substrate in region 16. The sample-hemocyte preparation-substrate mixture then traverses conduit 8 to optical cell 6. This type of cartridge may be used for performing, for example, an endpoint chromogenic assay or a multi-step kinetic chromogenic assay, as discussed in more detail below.

Depending upon the type of assay to be performed, a preselected amount of an agent representative of a microbial contaminant, or "spike," such as lipoteichoic acid, is disposed on first region 14 of the fluid contacting surface of one or more conduits 8. Alternatively, the spike may be disposed on a different region of the conduit 8.

The cartridges can be designed and used according to the type and/or number of tests required. For example, a single sample may be tested, for example, in duplicate or triplicate, for example, for research laboratory uses or for medical device and biopharmaceutical testing. Alternatively, two or more different samples may be tested individually, for example, for dialysis facility testing of water and dialysate. The cartridge preferably is a single-use, disposable cartridge that is discarded after one use. The cartridge can use approximately 20-100 fold less hemocyte preparation per sample than is used in the conventional endpoint chromogenic or kinetic chromogenic assays performed in multi-well plates, and thus provides a less costly and environmentally-friendly test. Once a particular assay format has been chosen, the cartridge may be fabricated as discussed below. All the reagents and materials used to prepare the cartridge preferably are free of the microbial contaminant for which the cartridge ultimately will be used to test. It is contemplated that the cartridge may be fabricated with any hemocyte preparation of choice.

Cartridge Fabrication

In fabricating an exemplary cartridge, it is helpful to combine the hemocyte preparation and phenol oxidase substrate with at least one resolubilizing agent, such as a sugar or salt, and at least one anti-flaking agent, such as a polymer, prior to drying the hemocyte preparation onto the solid support.

The resolubilizing agent preferably stabilizes the hemocyte preparation in the dried form and facilitates resolubilization of the reagents during the assay. Useful resolubilizing agents include, for example, mannitol, mannose, sorbitol, trehalose, maltose, dextrose, sucrose, and other monosaccharides and disaccharides. The hemocyte preparation and phenol oxidase substrate preferably contain from about 0.01% (w/v) to about 20% (w/v), more preferably from about 0.1% (w/v) to about 1.0% (w/v) of the resolubilizing agent prior to drying.

The anti-flaking agent is an agent that prevents or reduces the likelihood that the hemocyte preparation and/or phenol oxidase substrate becomes disassociated from a solid support in the form of a dry flake. The anti-flaking agent preferably also stabilizes the hemocyte preparation or phenol oxidase substrate in the dried form. Useful anti-flaking agents include, for example, one or more polymers, including, for example, polyethylene glycol, polyvinyl pyrolidone, dextrans, mannitol, and proteins, for example, serum albumin, hemolymph or hemocyanin. The lysate preferably contains from about 0.01% (w/v) to about 25% (w/v), more preferably from about 0.1% (w/v) to about 1.0% (w/v) of anti-flaking agent prior to drying.

In addition, it has been found that certain polymers reduce the formation of air bubbles (e.g., frothing) when the hemocyte preparation and/or phenol oxidase substrate are resolubilized. Useful anti-frothing agents include polyvinyl alcohol and polypropylene glycol. In order to reduce frothing, the hemocyte preparation and/or phenol oxidase substrate may contain from about 0.01% (w/v) to about 10% (w/v), more preferably from about 0.1% (w/v) to about 1.0% (w/v) anti-frothing agent prior to drying.

Figure 5A:
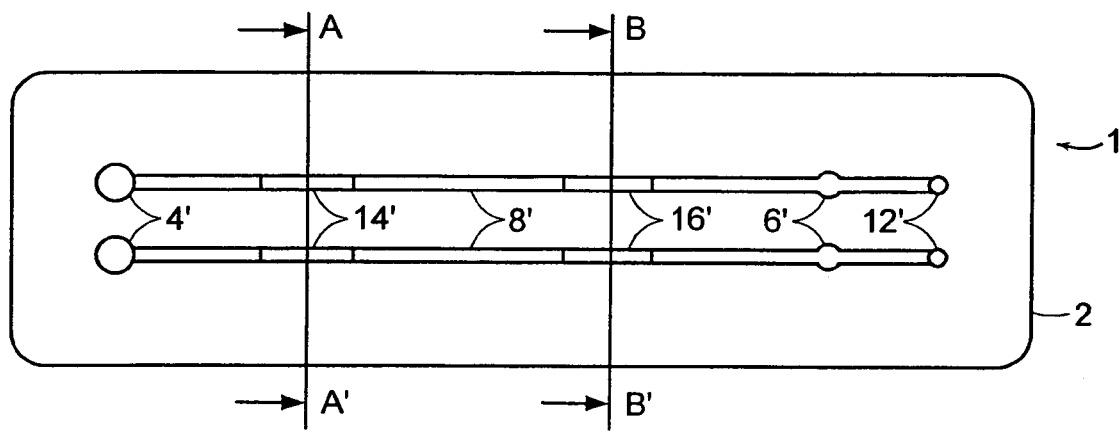
Figure 5B:
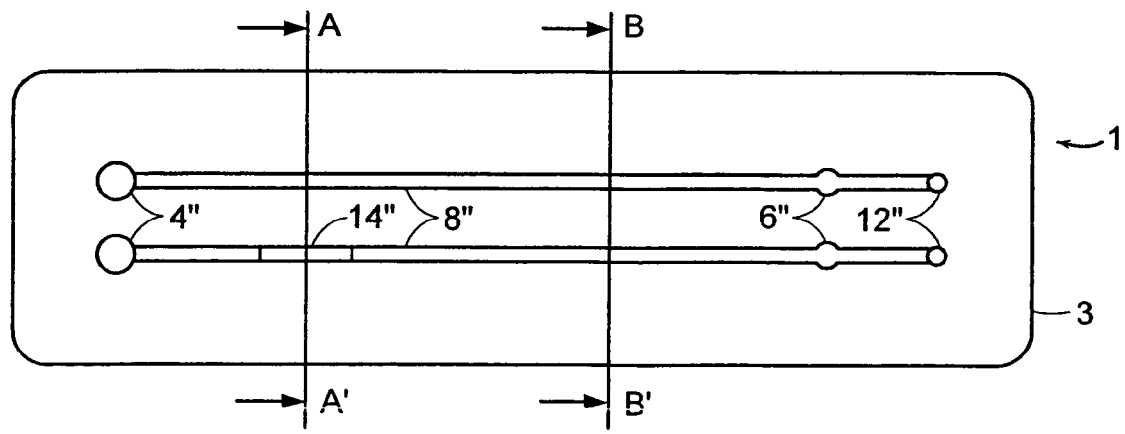

An exemplary fabrication process for the cartridge is described with reference to FIG. 5, in which FIG. 5A represents a bottom half 2 of cartridge 1 and FIG. 5B represents a top half 3 of cartridge 1. Once prepared, the two halves of the cartridge 1 are joined to one another by adhesive, solvent bonding, ultrasonic welding, snap fit joints, or the like.

In FIG. 5A, the bottom half 2 of the cartridge 1 defines one half of each conduit 8' (each having a first region 14' and a second region 16'). During fabrication of the bottom half 2 of the cartridge 1, a hemocyte preparation is applied to each first region 14' and chromogenic substrate is applied to each second region 16'. In FIG. 5B, the top half 3 of the cartridge 1 defines one half of each conduit 8". During fabrication of top half 3 of the cartridge 1, an agent representative of a microbial contaminant (i.e., a spike), for example, a preselected amount of lipoteichoic acid, can, depending on the assay, be applied to region 14". Once the reagents have been applied to the respective top 3 and bottom 2 halves of the cartridge 1, the cartridge halves 2 and 3 then are dried under conditions that preserve the activity of the hemocyte preparation and permit reconstitution of the hemocyte preparation to produce an active hemocyte preparation. In order to preserve the activity of the reagents during drying, the cartridge halves 2 and 3 are placed in an environment having a temperature from about 4° C. to about 40° C., more preferably, from about 10° C. to about 35° C., more preferably, from about 15° C. to about 30° C., and a relative humidity from about 0% to about 30%, more preferably, from about 2% to about 20%, more preferably from about 4% to about 10%. Drying conditions may include, for example, a temperature of about 25° C. and a relative humidity of about 5%. In an alternative approach, the hemocyte preparation may be dried via freeze drying under standard conditions, about −30° C. to about −40° C. under vacuum.

Figure 5C:
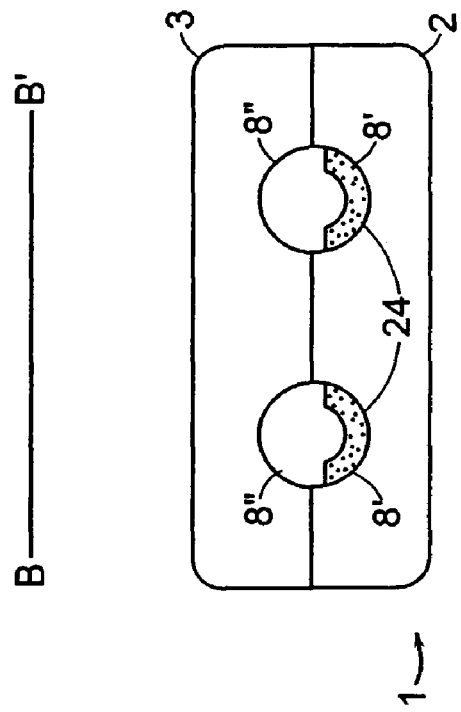
Figure 5D:
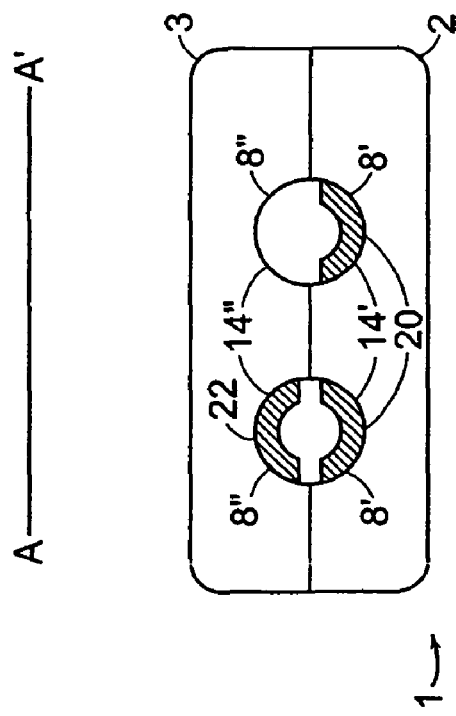

After drying, the two cartridge halves 2 and 3 are joined to one another to create an intact cartridge 1. FIG. 5C is a cross-sectional view through Section A-A' in which the two halves of the conduit (namely 8' and 8") together create an intact conduit 8, wherein region 14' of the bottom 8' of each conduit contains immobilized hemocyte preparation 20 and region 14" of the top 8" of one conduit contains immobilized lipoteichoic acid 22. FIG. 5D is a cross-sectional view through Section B-B' in which region 16' of the bottom 8' of each conduit contains immobilized phenol oxidase substrate 24.

The dimensions of a particular cartridge 1 may vary depending upon the number and/or type of assays to be performed. However, in one embodiment, as shown schematically in FIG. 4A, for example, the cartridge 1 has a length of about 10.16 cm (4.00"), width of about 2.54 cm (1.00"), and a height of about 0.476 cm (0.188"). The bore of the conduit 8 running from the fluid inlet port 4 to the optical cell 6 is about 0.127 cm (0.050"), where the hemocyte preparation is dried on a region 14 of the conduit 8 about 2.381 cm (0.938") from the fluid inlet port 4, and a phenol oxidase substrate is dried on a region 16 of the conduit 8 about 4.65 cm (1.831") from the fluid inlet port 4. The optical cell 6 in this embodiment is dimensioned to accommodate about 25 µL of sample.

Specimen Collection and Preparation

The cartridge may be used to determine the level of microbial contamination in a fluid, for example, a fluid to be administered locally or systemically, for example, parenterally to a mammal, or a body fluid to be tested for infection, including, for example, blood, lymph, urine, serum, plasma, ascites fluid, lung aspirants, and the like. In addition, the cartridge may be used to determine the level or microbial contamination in a water supply, for example, a supply of drinking water. In addition, the cartridge may be used to determine the level of microbial contamination in a food product, pharmaceutical, or medical device. Furthermore, the cartridge can be used to determine the level of microbial contamination on a surface. For example, the surface of interest is swabbed and then the swab is introduced into or dissolved in liquid. The liquid can then be assayed as usual.

In general, materials used to harvest, store, or otherwise contact a sample to be tested, as well as test reagents, should be free of microbial contamination, for example, should be pyrogen-free. Materials may be rendered pyrogen-free by, for example, heating at 250° C. for 30 minutes. Appropriate precautions should be taken to protect depyrogenated materials from subsequent environmental contamination.

Representative Assays that can be Performed in the Cartridge

It is contemplated that a variety of hemocyte preparation-based assays may be used in the cartridge, such as, for example, an endpoint chromogenic assay, a single-step kinetic assay, and a multi-step kinetic assay.

1. Endpoint Chromogenic Assay

The endpoint chromogenic assay is described in Prior (1990) supra, pp. 28-34, and U.S. Pat. Nos. 4,301,245 and 4,717,658. Briefly, the endpoint chromogenic assay includes the steps of (i) solubilizing a hemocyte preparation with a sample to be analyzed, (ii) incubating the resulting mixture at a temperature of about 0° C. to about 40° C., preferably about 25° C. to about 40° C., for a predetermined time, (iii) contacting a test device containing substrate, for example, a phenol oxidase substrate, with the incubated sample-hemocyte preparation mixture, (iv) adding a reaction inhibitor, and (v) measuring, e.g., by colorimetric change, a substance produced from the substrate by enzymatic activity.

Figure 4A:
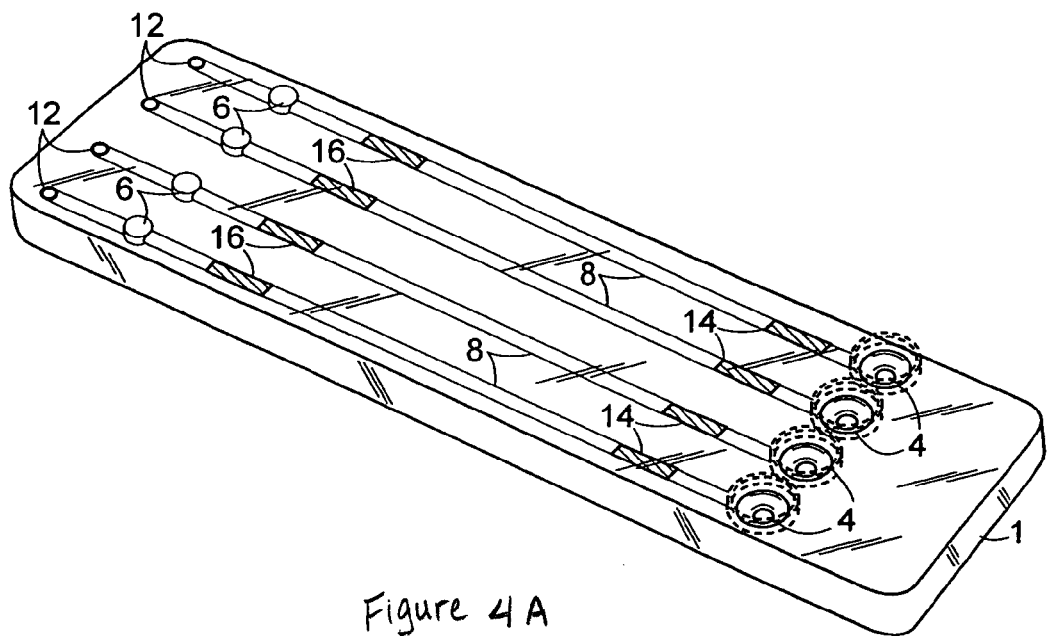
FIGS. 4A-4D are schematic illustrations of an exemplary cartridge useful in practicing methods of the invention in perspective view (FIG. 4A), top view (FIG. 4B), side view (FIG. 4C), and end view (FIG. 4D)
Figure 4B:
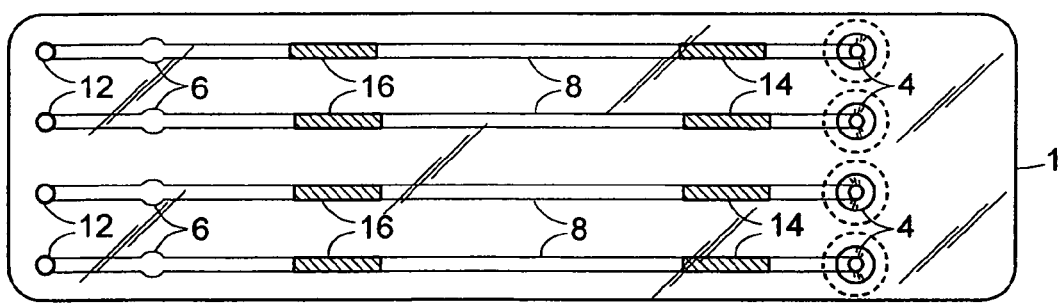
Figure 4C:
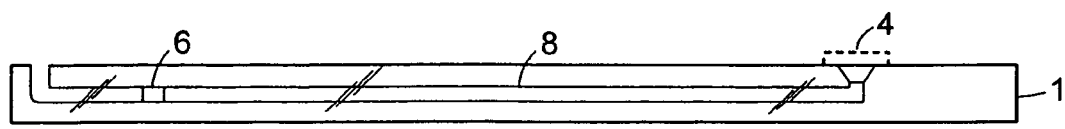
Figure 4D:
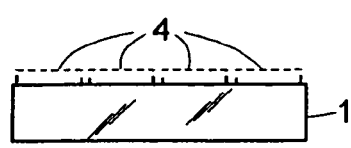

Referring to FIG. 4A, in order to perform an endpoint chromogenic assay in a cartridge 1, a sample is moved, for example, to a first region 14 of the conduit 8 containing the hemocyte preparation, where it is solubilized, for example, by cycling between forward and reverse pump action. Following a predetermined incubation period, the sample-hemocyte preparation mixture then is moved, for example, by pump action to a second region 16 of the conduit 8 containing the phenol oxidase substrate, where it is solubilized, for example, by cycling between forward and reverse pump action. The sample-hemocyte preparation-substrate mixture then is moved to a third region containing a reaction inhibitor. Afterwards, the sample-hemocyte preparation-substrate mixture is moved to optical cell 6 for measurement of an optical property, for example, the absorbance or transmittance properties of the sample by an optical detector. The optical property of the sample-hemocyte preparation-substrate mixture at a certain predetermined time point can then be interpolated onto a predetermined standard curve, for example, showing absorbance, optical density, or transmittance on the Y axis versus lipoteichoic acid concentration on the X axis, to give the concentration of the microbial contaminant in the sample.

2. Single-Step Kinetic Assay

A single-step kinetic assay, for example, a single step-chromogenic assay, is described in U.S. Pat. No. 5,310,657. Briefly, the kinetic chromogenic assay includes the steps of (i) simultaneously solubilizing a hemocyte preparation with a sample to be analyzed and a substrate, for example, phenol oxidase substrate, (ii) incubating the resulting mixture at a temperature of about 0° to about 40° C., preferably about 25° to about 40° C., over a predetermined time range, and (iii) measuring a time required for a calorimetric change to reach a pre-selected value or change of the colorimetric readout, using a conventional spectrophotometer.

Referring to FIG. 4A, in order to perform a kinetic chromogenic assay in a cartridge 1, a sample is moved, for example, by pump action, to a first region 14 of the conduit 8 containing both the hemocyte preparation and substrate, where it is solubilized, for example, by cycling between forward and reverse pump action. The sample-hemocyte preparation-substrate mixture then is moved to optical cell 6 for measurement of an optical property, for example, the absorbance or transmittance properties of the sample by an optical detector. The detector may determine how long it takes for each optical property to exhibit, for example, a 5% drop in optical transmittance. Results from multiple assays, for example, two assays, can be averaged. The resulting values may then be interpolated onto a predetermined standard curve, for example, showing the time for a preselected change in absorbance or transmittance (as the case may be) on the Y axis versus lipoteichoic acid concentration on the X axis, to give the concentration of the contaminant in the sample.

3. Multi-Step Kinetic Assay

Figure 6:
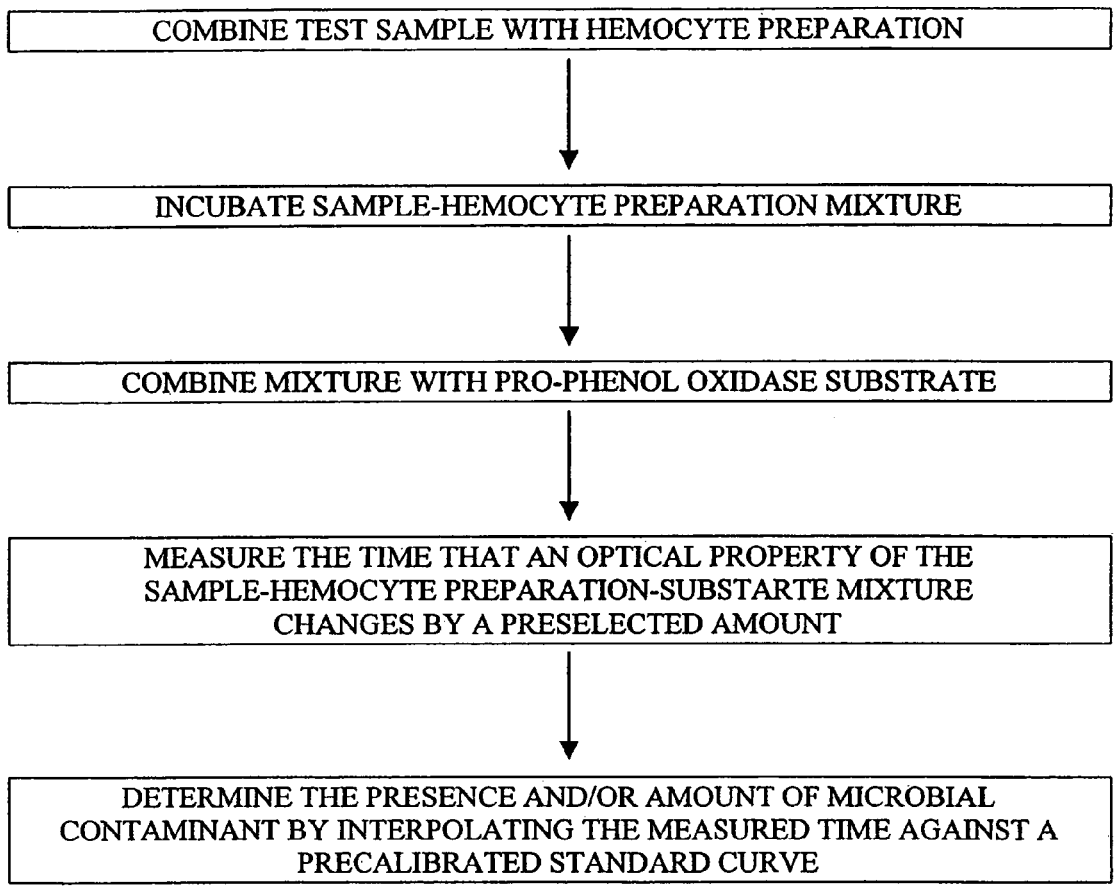
FIG. 6 is a flow chart for an exemplary multi-step kinetic chromogenic assay.

As will be discussed in more detail, the cartridge may also be used to perform a multi-step kinetic assay. The various steps involved in the multi-step kinetic assay are shown schematically in FIG. 6. The assay is initiated by combining the sample to be tested with a volume of a hemocyte preparation to produce a sample-hemocyte preparation mixture. The mixture then is incubated for a predetermined period of time. The mixture then is contacted with a substrate, for example, a phenol oxidase substrate, to produce a sample-hemocyte preparation-substrate mixture. Thereafter, the time in which a preselected change in an optical property (for example, a specific change in an absorbance value or a specific change in a transmission value) is measured. The presence and/or amount of microbial contaminant may be then determined by interpolating the measured time against a pre-calibrated standard curve, for example, a standard curve showing the time to make a preselected change in optical property (absorbance or transmittance) on the Y axis versus lipoteichoic acid concentration on the X axis.

The standard curve may be created, for example, by adding increasing amounts of an agent, for example, lipoteichoic acid, in a blank sample, for example, pyrogen-free water. The time for which a preselected change in an optical property, for example, a preselected increase in absorbance or a preselected decrease in transmittance, is determined for each concentration of lipoteichoic acid. The various time measurements to achieve a standard change in optical property then are plotted as a function of the lipoteichoic acid concentration. In general, the concentration of lipoteichoic acid is inversely proportional to the time necessary to achieve the standard change in optical property. The standard curve can then be used to assess the presence and/or amount of lipoteichoic acid in the sample of interest.

As will be apparent to one skilled in the art, the relative amounts of hemocyte preparation and phenol oxidase substrate can be adjusted to ensure that effective amounts of these two components are present in the sample-hemocyte preparation-substrate mixture at the end of the assay. The final amount of hemocyte preparation protein in the assay is from about 1 µg to about 500 µg, preferably about 20 µg. The final amount of the substrate, for example, the phenol oxidase substrate in the assay is from about 1 µg to about 50 µg, preferably about 6.5 µg. The determination of the concentration and composition of the substrate, for example, the phenol oxidase substrate, is considered to be within the level of skill in the art.

The final volume of the resulting sample-hemocyte preparation-substrate mixture can be based on the requirements of the optical detector used to measure the change in optical property of the sample. The ratio of volumes between the sample, lysate, and substrate can be readily established by those of ordinary skill in the art. Depending on the relative volumes of the sample, hemocyte preparation, and substrate in the sample-hemocyte preparation-substrate mixture, the concentration of the other components of the assay can be adjusted to maintain the final concentrations in the operable range, as described herein.

Referring to FIG. 4A, to perform the multi-step kinetic assay in an exemplary cartridge 1, a sample is first moved, for example, by pump action, to a first region 14 containing the hemocyte preparation, where it is mixed and incubated for a predetermined period of time. The sample-hemocyte preparation mixture then is moved, for example, by pump action, to the second region 16 containing the substrate, for example, the phenol oxidase substrate, where it is solubilized. The sample-phenol oxidase-substrate mixture then is moved to optical cell 6, for a measurement of an optical property. The time intervals required for mixing and incubating steps are preprogrammed for optimal sensitivity and microbial contaminant concentration range.

It is understood that a spiked sample can be assayed in parallel with an unspiked sample. The microbial contaminant concentration in the unspiked sample and the microbial contaminant recovered in the spiked sample can be compared to determine the presence of interference, such as an inhibitor or an enhancer of the reaction, as previously described.

Although the multi-step assay may be performed in a cartridge of the type discussed above, it may be employed in a variety of other formats, for example, within the well of a microtiter plate. Multiple samples of various test fluids, as well as spiked samples and the series of control samples making up a standard curve, may be placed in the wells of the microplate. Fixed amounts of hemocyte preparation and phenol oxidase substrate are added to each of the wells, preferably using an automated system, such as a robot, and the plate processed by a microplate reader, which can be programmed to sequentially read the absorbance of each well in a repetitive fashion.

EXAMPLES

Practice of the invention will be more fully understood from the following non limiting examples, which are presented herein for illustrative purposes only, and should not be construed as limiting the invention in any way.

Example 1

Preparation of Lipoteichoic Acid Reactive Material from *Cancer borealis*

A preparation of lipoteichoic acid reactive material was made from *Cancer borealis* hemocytes by the following method.

The appearance of the crab was observed and recorded. Centrifuge tubes (50 mL) were labeled and placed on ice. A sterile 18 gauge needle was connected to the syringe in a sterile manner, and the syringe was filled with 5 mL of Bleed Solution (0.45 M sodium chloride, 0.1 M glucose, 30 µM sodium citrate, 26 µM citric acid, and 2.5 µM sodium EDTA, pH 4.6). The interior unsclerotized membrane of one of the crab's hind most legs was washed with 70% ethanol and dried with a sterile wipe. The needle was carefully inserted into the interior unsclerotized membrane of one of the washed hind legs. The crab was lifted above the needle and the syringe gently pulled to elicit blood flow. If no blood flowed into the syringe, the position of the needle was adjusted (e.g., moved deeper into the membrane). At least 20-60 mL of blood was obtained from each crab. When the syringe was full or blood no longer flowed, the needle was removed from the syringe and the blood gently transferred to a centrifuge tube.

Additional Bleed Solution was added to make a blood: Bleed Solution ratio of 2:1, mixed gently and kept on ice. For example, if 20 mL of blood was collected, 10 mL of Bleed Solution was added in total (5 mL Bleed Solution already added to the syringe plus an additional 5 mL of Bleed Solution).

The above method was performed on each crab with a fresh needle, keeping the same syringe for all crabs but filling the syringe with 5 mL of Bleed Solution with each new crab. All the tubes were centrifuged at 3,000 rpm in a RC-3B refrigerated centrifuge (Sorvall, a division of Kendro Laboratories, Asheville, N.C.) at 10° C. for 5 minutes. The lymph supernatant was discarded or saved in a clean container for further extraction. A 50% bleed volume of Wash Solution (0.45 M sodium chloride, 0.1 M glucose, 0.1 M cacodylic acid, pH 7.0) was added to the cell pellet (e.g., 10 mL of Wash Solution was added to a pellet obtained from 20 mL of blood), and the pellet was gently resuspended using a pipette. The tubes were centrifuged at 3,000 rpm in a RC-3B refrigerated centrifuge (Sorvall, a division of Kendro Laboratories, Asheville, N.C.) at 10° C. for 5 minutes. The Wash Solution was discarded and a 10% bleed volume of Release Solution (0.45 M sodium chloride, 0.1 M glucose, 0.1 M cacodylic acid, 3 µM calcium ionophore C7522 (Sigma Chemical Co., St. Louis, Mo.), 5 µM calcium chloride, pH 7.0) was added to the pellet (e.g., 2 mL of Release Solution was added to a pellet prepared from 20 mL of blood). The pellet was gently resuspended using a pipette. The resulting solution was vortexed carefully for about 1-2 seconds and incubated for 1 hour at room temperature. The tubes then were centrifuged at 3,000 rpm in a RC-3B refrigerated centrifuge at 10° C. for 5 minutes and the supernatant was transferred to new tubes for testing.

Once the pro-phenol oxidase activity of the lysate was determined, the resulting preparation was either used freshly in an assay, lyophilized, dried on a solid support (for example, a cartridge) or aliquoted into tubes (for example, 1-2 mL tubes and frozen at either −20° C. to −80° C.) until use.

Example 2

Protocol for Lipoteichoic Acid Assay

In this assay, a single-step kinetic assay was performed in a microtiter plate. In this assay, lipoteichoic acid (LTA) (L2515, Sigma Chemical Co., St. Louis, Mo.), was diluted to give a standard curve. The standard curve contained 3 fold serial dilutions starting from 60 µg/mL to 0.74 µg/mL in 0.2 M Tris buffer pH 7.4. Tris buffer (0.2 M, pH 7.4) was used as a negative control. Comparable standard curves were also created using peptidoglycan (77140, Fluka, Switzerland), glucan (glucan standard, Charles River Endosafe, Charleston, S.C.) and lipopolysaccharide (L-2637, Sigma Chemical Co., St. Louis, Mo.).

The *C. borealis* preparation used in this Example was prepared essentially as described in Example 1. However, the supernatant prior to testing for pro-phenyl oxidase activity was further purified as follows. Briefly, the supernatant was harvested and an equal volume of a saturated solution of ammonium sulfate was added to the supernatant and mixed gently. Then, the mixture was incubated on ice for 1 hour on ice, and was then centrifuged in a RC-3B refrigerated centrifuge at 10° C. for 5 minutes. The resulting pellet was harvested and resuspended in an amount of distilled water equivalent to the volume of supernatant initially combined with the saturated ammonium sulfate. The resulting preparation can then be tested for pro-phenyl oxidase activity.

The lipoteichoic acid, peptidoglycan, glucan and lipopolysaccharide standards and controls were added to appropriate wells (120 µL per well). Then, 15 µL of the *C. borealis* hemocyte preparation was added to each well. 10 µL of isoprenaline sulfate substrate ((I0261, TCI-GR, Tokyo, Japan) 16 mM in clean water) was then added to each well and gently mixed by shaking for 3-5 seconds. The absorbance of each well was read periodically (i.e., kinetically) at 490 nm at 37° C. for 40-60 minutes (Min OD: 0, Max OD: 0.4, Onset OD: 0.05). The results were reported in optical density units and shown in FIG. 7.

Figure 7:
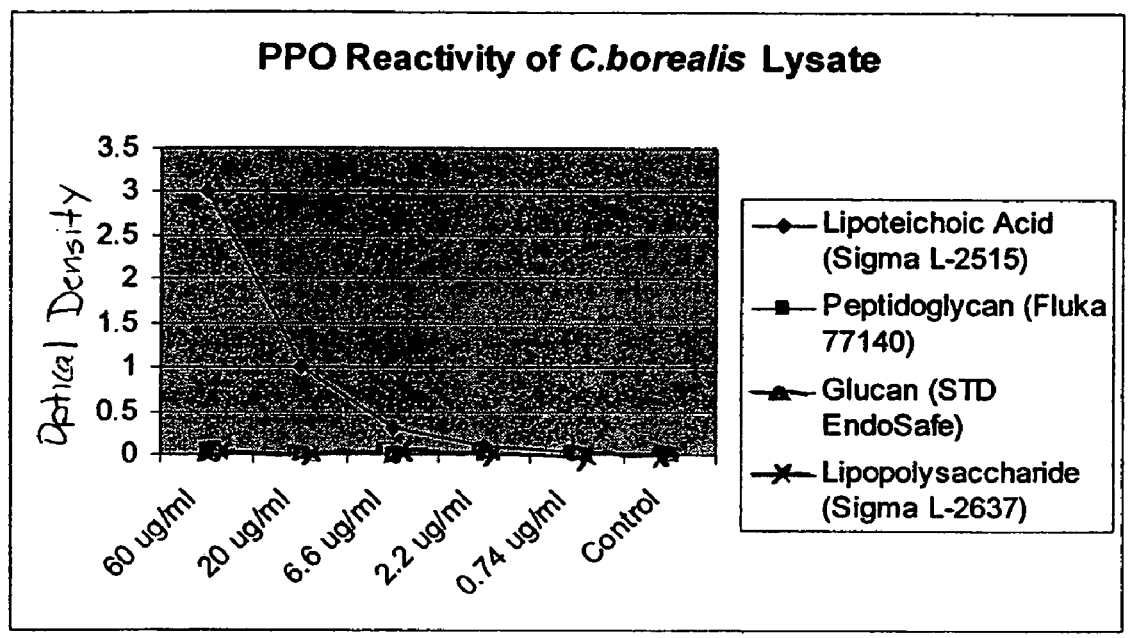
FIG. 7 is a graph showing pro-phenol oxidase reactivity in a *Cancer borealis* hemocyte preparation in the presence of lipoteichoic acid, peptidoglycan, glucan and lipopolysaccharide.

FIG. 7 shows that the *Cancer borealis* preparation was activated by lipoteichoic acid ranging in concentration from 60 µg/mL to less than 2.2 µg/mL. In contrast, peptidoglycan, glucan, and lipopolysaccharide did not activate the *Cancer borealis* preparation at the concentrations tested. These results show that, under the appropriate conditions, the *Cancer borealis* preparation can specifically detect lipoteichoic acid.

Example 3

Use of *Cancer borealis* Hemocyte Preparation for the Detection of Gram Positive Bacteria In this Example, a *Cancer borealis* preparation produced according to Example 1 was used to detect the presence of Gram positive bacteria in test samples. In particular, in this Example, the reactivity of the preparation was tested against various Gram positive bacteria (including, *Staphylococcus epidermidis*, *Bacillus subtilis*, *Bacillus pumilus*, *Bacillus megaterium* and *Deinococcus radiodurans*), Gram negative bacteria (including, *Escherichia coli*, *Pseudomonas stutzeri*, *Sphingomonas subarctica*), Actinomyces (including *Nocardiopsis antartica*), and fungi (*Aureobasidium pullulans*).

In this example, the reactivity was assessed using a single-step kinetic assay implemented in a microtiter plate. In this assay, lipoteichoic acid (LTA) (L2515, Sigma Chemical Co., St. Louis, Mo.), was diluted to give a standard curve. The standard curve contained 5 fold serial dilutions starting from 100 µg/mL to 0.032 µg/mL in Vasse Media (5.5 mM D-(+)-Glucose, 40 mM Potassium Phosphate (dibasic), 15 mM Potassium Phosphate (monobasic), 0.4 mM Magnesium Sulfate, 7.5 mM Ammonium Sulfate, 2 mM Citric Acid, Tryptone (10 g/L), pH 7.0). Vasse Media, pH 7.0, was used as a negative control. Comparable 10 fold curves were also created using lipopolysaccharide (L-2637, Sigma Chemical Co., St. Louis, Mo.), *Staphylococcus epidermidis* (Vasse Media, Tryptic Soy Broth), *Bacillus subtilis* (Vasse Media, Tryptic Soy Broth), *Bacillus megaterium* (Vasse Media, Tryptic Soy Broth), *Bacillus pumilus* (Tryptic Soy Broth), *Deinococcus radiodurans* (Tryptic Soy Broth), *Escherichia coli* (Tryptic Soy Broth), *Pseudomonas stutzeri* (Tryptic Soy Broth), *Sphingomonas subarctica* (Tryptic Soy Broth), *Nocardiopsis antartica* (Tryptic Soy Broth), and *Aureobasidium pullulans* (Tryptic Soy Broth).

The lipoteichoic acid standard, lipopolysaccharide and bacterial samples and controls were added to appropriate wells (120 µL per well). Wells of the microplate contained 10 µL of dried *Cancer borealis* hemocyte preparation. Then, 10 µL of isoprenaline sulfate substrate ((I0261, TCI-GR, Tokyo, Japan) 16 mM in clean water) was added to each well. The absorbance of each well was read periodically (i.e., kinetically) at 490 nm at 37° C. for 90 minutes (Min OD: 0, Max OD: 1.0, Onset OD: 0.1).

Figure 8:
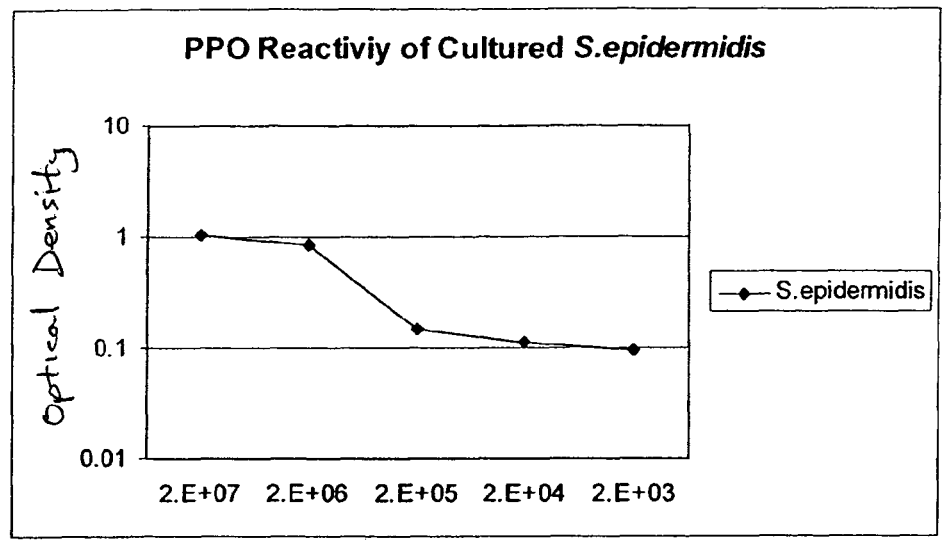
FIG. 8 is a graph showing the pro-phenol oxidase reactivity of Cancer borealis hemocyte preparation in the presence of *Staphylococcus epidermidis* (Gram positive) bacterial cells.

The results are reported as the change in optical density as a function of cell density. The reactivity of the preparation against different numbers of cells of the Gram positive organism *Staphylococcus epidermis* (expressed in optical density units per cell number) is listed in Table 1 and shown graphically in FIG. 8. The results show that the *Cancer borealis* preparation can detect less than $2 \times 10^3$ cells/mL of *Staphylococcus epidermis*.

TABLE 1

| Cell Number/mL | Optical Density Units/mL |
| --- | --- |
| $2 \times 10^7$ | 1.021 |
| $2 \times 10^6$ | 0.852 |
| $2 \times 10^5$ | 0.146 |
| $2 \times 10^4$ | 0.111 |
| $2 \times 10^3$ | 0.096 |

Figure 9:
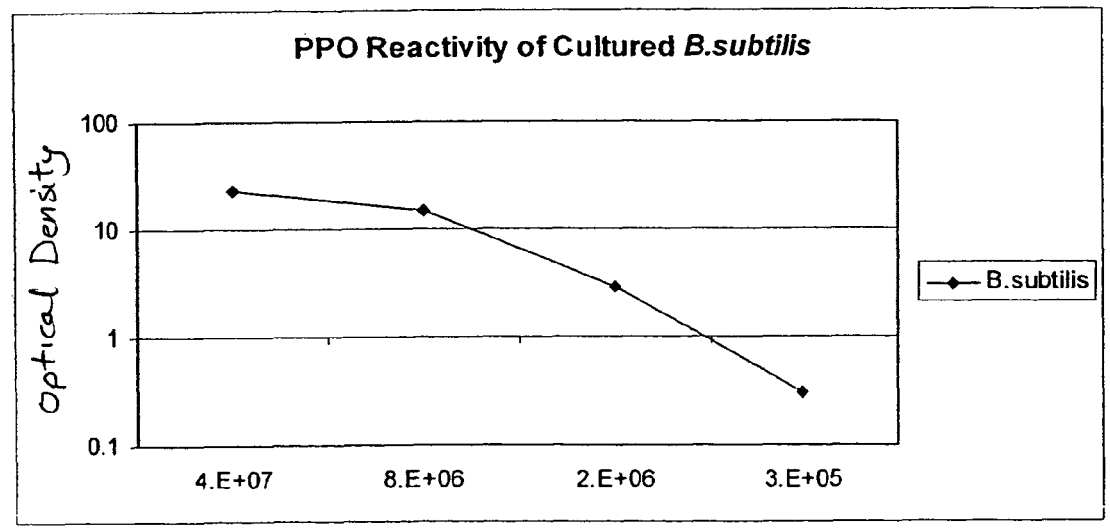
FIG. 9 is a graph showing the pro-phenol oxidase reactivity of Cancer borealis hemocyte preparation in the presence of *Bacillus subtilis* (Gram positive) bacterial cells.

The reactivity of the preparation against different numbers of cells of the Gram positive organism, *Bacillus subtilis*, (expressed in optical density units per cell number) is listed in Table 2, and shown graphically in FIG. 9. The results show that the *Cancer borealis* preparation can detect between $3 \times 10^5$ and $6 \times 10^4$ cells/mL of *Bacillus subtilis*.

TABLE 2

| Cell Number/mL | Optical Density Units/mL |
| --- | --- |
| $4 \times 10^7$ | 22.66 |
| $8 \times 10^6$ | 14.96 |
| $2 \times 10^6$ | 2.97 |
| $3 \times 10^5$ | 0.3 |
| $6 \times 10^4$ | 0 |
| Control | 0 |

The reactivity of the *Cancer borealis* preparation against a number of Gram positive bacteria, Gram negative bacteria, fungi, and actinomycetes is summarized in Table 3.

The results show that the *Cancer borealis* preparation detected all of the Gram positive organisms. In contrast, the *Cancer borealis* preparation did not detect either the Gram negative bacteria or the fungus *Aureobasidium pullulans*. Although, the *Cancer borealis* preparation detected the presence of the actinomycetes, *Nocardiopsis antartica*, this organism stains like the Gram positive bacteria.

TABLE 3

| Organism Name | Type of Organism | Cell Concentration | Optical Density Units |
| --- | --- | --- | --- |
| Bacillus subtilis | Gram Positive bacteria | $2 \times 10^6$ | 1.188 |
| Bacillus pumilus | Gram Positive bacteria | $4.7 \times 10^7$ | 2.238 |
| Bacillus megaterium | Gram Positive bacteria | $3.5 \times 10^7$ | 2.577 |
| Bacillus species | Gram Positive bacteria | $3 \times 10^6$ | 1.053 |
| Deinococcus radiodurans | Gram Positive bacteria | $2.1 \times 10^6$ | 2.019 |
| Escherichia coli | Gram Negative bacteria | $1 \times 10^9$ | 0 |
| Pseudomonas stutzeri | Gram Negative bacteria | $2.9 \times 10^8$ | 0 |
| Sphingomonas subarctica | Gram Negative bacteria | $1.9 \times 10^7$ | 0 |
| Nocardiopsis antartica | Actinomyces | $1 \times 10^5$ | 1.453 |
| Aureobasidium pullulans | Fungi | $4.8 \times 10^6$ | 0 |

Example 4

Preparation of Lipoteichoic Acid Reactive Material from *Limulus polyphemus*

This Example demonstrates that *Limulus polyphemus* hemocytes contain lipoteichoic acid reactive material capable of detecting the presence of Gram positive bacteria. Blood was collected from *Limulus polyphemus* and the lipoteichoic acid reactive material was produced as described in Example 1.

The resulting preparation then was tested for reactivity against lipoteichoic acid, lipopolysaccharide and glucan. This assay was a two-step kinetic assay, perfromed in a microtiter plate. In this assay, lipoteichoic acid (LTA) (L2515, Sigma Chemical Co., St. Louis, Mo.), was diluted to give a standard curve. The standard curve contained 10 fold serial dilutions starting from 100 µg/mL to 0.01 µg/mL in 0.2 M Tris buffer pH 7.4. Tris buffer (0.2 M, pH 7.4) was used as a negative control. Comparable standard curves were also created using glucan (glucan standard, Charles River Endosafe, Charleston, S.C.) and lipopolysaccharide (L-2637, Sigma Chemical Co., St. Louis, Mo.).

The lipoteichoic acid, peptidoglycan, glucan, lipopolysaccharide standards and controls then were added to the appropriate wells (100 µL per well). Then, 10 µL of *Limulus* hemocyte preparation was added to each well and gently mixed by shaking for 3-5 seconds. Then, the microplate was incubated at 37° C. for 20 minutes. Then, 10 µL of isoprenaline sulfate substrate ((10261, TCI-GR, Tokyo, Japan) 4 mM in clean water) was added to each well and gently mixed by shaking for 3-5 seconds. The absorbance of each well was read periodically (i.e., kinetically) at 490 nm at 37° C. for 90 minutes (Min OD: 0, Max OD: 0.4, Onset OD: 0.05). The results expressed as a change in optical density (+) or no change in optical density (−) are summarized in Table 4. These results demonstrate that the *Limulus* preparation is capable of detecting lipoteichoic acid. The results also demonstrate that the *Limulus* preparation is also capable of detecting lipopolysaccharide and glucan.

TABLE 4

| Concentration | Lipoteichoic acid | Lipopolysaccharide | Glucan |
|---|---|---|---|
| 100 µg/ml | + | + | + |
| 10 µg/ml | + | + | + |
| 1 µg/ml | + | − | − |
| 100 ng/ml | − | − | − |
| 10 ng/ml | − | − | − |
| Control | − | − | − |

Example 5

Preparation of Cartridge for Use with *Cancer borealis* Preparation in a Two-Step Kinetic Assay In this Example, a *Cancer borealis* preparation from Example 1 was incorporated into a cartridge and used in a two-step kinetic assay. The reactivity of the *C. borealis* preparation to different concentrations of lipoteichoic acid (LTA) (L2515, Sigma Chemical Co., St. Louis, Mo.) (0 µg/mL, 5.6 µg/mL, 16.7 µg/mL and 50 µg/mL) was tested in the cartridge using The Endosafe—PTS (Portable Test System) (Charles River Laboratories, Charleston, S.C.).

*Cancer borealis* hemocyte preparation was dried in the cartridge as described above in the Cartridge Fabrication section. Mannitol (1%) and polyvinyl alcohol (0.1%) were added to a dilute form of *Cancer borealis* hemocyte preparation (diluted 1:2 in pyrogen free water) and then 5 µL of this solution was placed in the appropriate location in the cartridge for drying.

A cartridge of the type shown in FIG. 4 was prepared as follows. Referring to FIG. 5A, the *Cancer borealis* preparation and isoprenaline sulfate substrate was applied to regions 14' and 16', respectively, of conduit 8' of the bottom half 2 of the cartridge 1 using a Hamilton Microlab 540B Dispenser (Hamilton Company, Reno, Nev.). Briefly, 5 µL of a dilute *Cancer borealis* preparation (1:2 in pyrogen free water with mannitol (1%) and polyvinyl alcohol (0.1%)) was applied to region 14'. 5 µL of isoprenaline sulfate substrate ((10261, TCI-GR, Tokyo, Japan) 6 mM in clean water, 1% Mannitol and 0.1% polyvinyl alcohol) was applied to region 16'. The bottom half 2 of the cartridge 1 was dried under a controlled temperature of 25° C.+/−2° C. and a humidity of 5%+/−5% in a Lunaire Environmental Steady State & Stability Test Chamber (Lunaire Environmental, Williamsport, Pa.) in a Puregas HF200 Heatless Dryer (MTI Puregas, Denver, Colo.) for 1 hour. Temperature and humidity was controlled by a Watlow Series 96 1/16 DIN Temperature Controller (Watlow Electric Manufacturing Company, St. Louis, Mo.).

Referring to FIG. 5B, a top half of the cartridge was prepared without a spike (lipoteichoic acid) applied to region 14" of the conduit 8" of the top half 3 of the cartridge 1. Following fabrication, the two halves 2 and 3 were assembled such that regions 14' and 14" were aligned one on top of the other, and the edges of the cartridge halves 2 and 3 were ultrasonically sealed using a Dukane Model 210 Ultrasonic Sealer (Dukane Corporation, St. Charles, Ill.) under the control of a Dukane Dynamic Process Controller (Dukane Corporation, St. Charles, Ill.).

Figure 10:
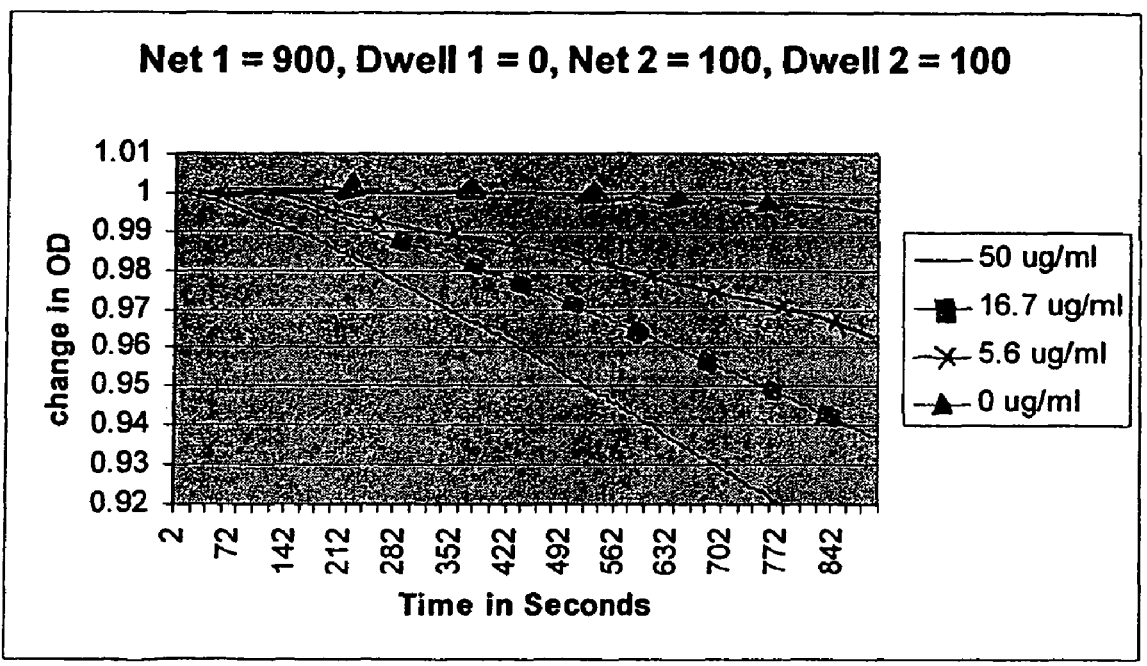
FIG. 10 is a graph showing the change in optical density over time in a cartridge-based two-step kinetic assay when a *Cancer borealis* hemocyte preparation is incubated with different concentrations of lipoteichoic acid.

The results are summarized in FIG. 10 and show that the *Cancer borealis* preparation has no reactivity in the absence of lipoteichoic acid. The reactivity of the preparation, however, increased the presence of increasing concentrations of lipoteichoic acid. These results demonstrate that the *Cancer borealis* preparation is capable of detecting lipoteichoic acid present in or on Gram positive bacteria.

Example 6

A Hemocyte-Based Preparation Capable of Detecting Gram Positive Bacteria, Gram Negative Bacteria and Fungi and Molds The *Cancer borealis* preparation made in accordance with the teachings of Example 1 is capable of detecting the presence of Gram positive bacteria but not Gram negative bacteria, yeasts and molds. To the extent that a preparation capable of detecting Gram positive bacteria, Gram negative bacteria, and yeasts and molds is desirable, it is possible to create such a preparation by combining the *Cancer borealis* preparation of Example 1 (reactive with Gram positive bacteria) with crude *Limulus amebocyte* lysate (reactive with Gram negative bacteria and yeast and molds).

Briefly, a crude *Limulus amebocyte* lysate prepared as originally described in Levin et al. ((1968) THROMB. DIATH. HAEMORRH. 19: 186) was combined in an equal amount with the *Cancer borealis* preparation prepared according to Example 1.

In this assay, a single-step kinetic assay was performed in a microtiter plate and lipoteichoic acid (LTA) (L2515, Sigma Chemical Co., St. Louis, Mo.) was diluted to give a standard curve. The standard curve contained 5 fold serial dilutions starting from 100 µg/mL to 1.28 ng/mL in Tris buffer (0.2 M, pH 7.4). Tris buffer (0.2M, pH 7.4) was used as a negative control. Comparable 5 fold curves were also created using peptidoglycan (77140, Fluka, Switzerland), glucan (glucan standard, Charles River Endosafe, Charleston, S.C.) and lipopolysaccharide (L-2637, Sigma Chemical Co., St. Louis, Mo.).

Figure 11:
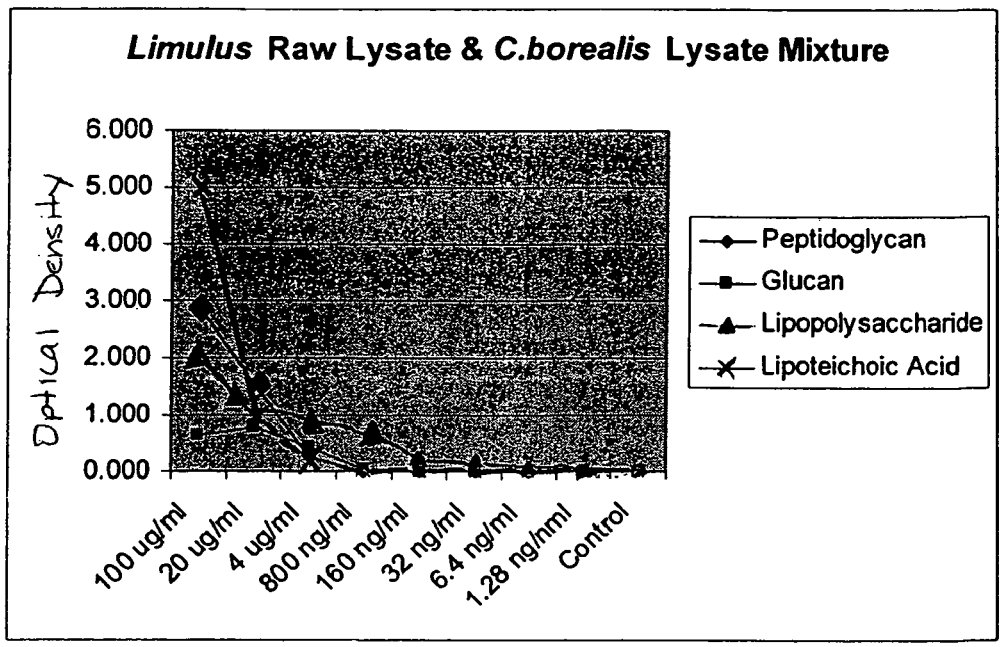
FIG. 11 is a graph showing the pro-phenol oxidase reactivity of a Cancer borealis hemocyte preparation combined with crude *Limulus amebocyte* lysate in the presence of peptidoglycan, glucan, lipopolysaccharide and lipoteichoic acid.

The lipoteichoic acid standard, peptidoglycan, glucan, lipopolysaccharide and controls then were added to the appropriate wells (120 µL per well). Wells of the microplate contained 5 µL of dried *C. borealis* hemocyte preparation. 5 µL of crude *Limulus amebocyte* lysate preparation then was added to the wells. Finally, 10 µL of isoprenaline sulfate substrate ((10261, TCI-GR, Tokyo, Japan) 16 mM in clean water) was added to each well. The absorbance of each well was read periodically (i.e., kinetically) at 490 nm at 37° C. for 150 minutes (Min OD: 0, Max OD: 1.5, Onset OD: 0.2). The results are summarized in FIG. 11 and show that the preparation reacts with lipopolysaccharide, peptidoglycan, glucan and lipoteichoic acid. These data suggest that such lysates can detect Gram positive bacteria, Gram negative bacteria and yeasts and fungi.

Example 7

Lipoteichoic Assays Using Fluorescent Substrates for Phenol Oxidase

This Example shows that a fluorescent phenol oxidase substrate can be used in a single-step kinetic assay in a well type format.

The assay was performed as follows. *Cancer borealis* lipoteichoic acid reactive material was produced as described in Example 1. 10 µL of the *Cancer borealis* preparation (1% mannitol) was dried into each well of a microtiter plate. Serial dilutions of lipoteichoic acid were prepared in 0.2 M Tris buffer (pH 7.4). Then, 120 µL of the lipoteichoic acid standards were added to the wells to give a pair of wells having a final concentration of 100 µg/mL, 50 µg/mL, 25 µg/mL, and 12.5 µg/mL. The control only contained 120 µL of Tris buffer. The plate was incubated at 37° C. for 30 minutes. Then, 20 µL of 2',7'-dichlorodihydrofluorescein diacetate (DCFDA) (D-399, Molecular probes, Eugene, Oreg.) and 8 mM catechol (C-9510, Sigma Chemical Co., St. Louis, Mo.) was added to one well of the pair. 20 µL of DCFDA, 8 mM catechol and 1/250 dilution of esterase (E-2884, Sigma Chemical Co., St. Louis, Mo.) was added to one well of the pair of wells. Absorbance at 490 nm was recorded for 120 minutes. The results, expressed in fluorescence units versus concentration of lipoteichoic acid, are presented in FIG. 12.

Figure 12:
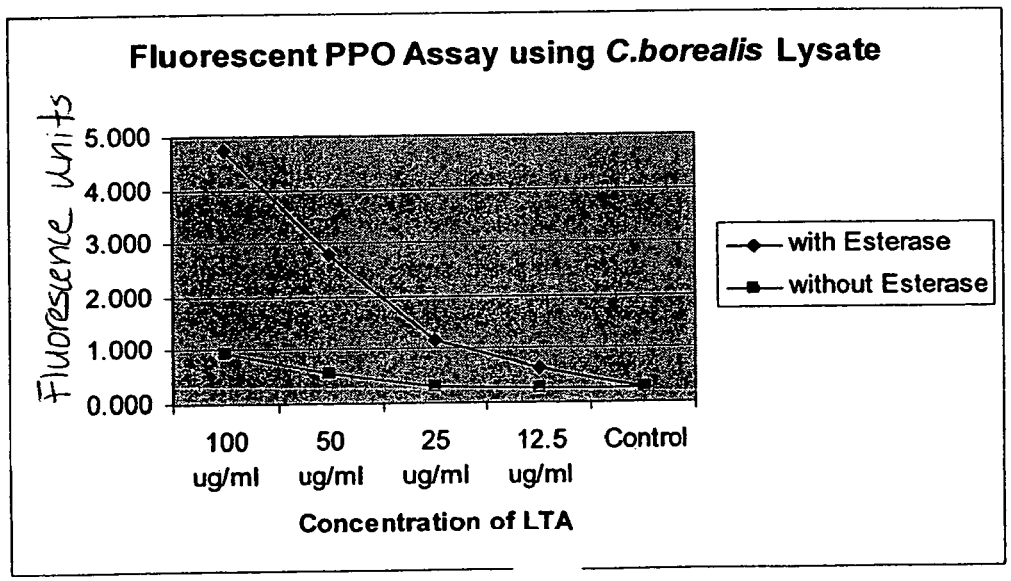
FIG. 12 is a graph showing the pro-phenol oxidase reactivity of Cancer borealis preparation in a multi-step kinetic assay using a fluorescent phenol oxidase substrate in the presence or absence of an esterase.

FIG. 12 shows that a fluorescent substrate can be used in an assay. The results show that although the assay can work in the presence and absence of the esterase, the assay is more sensitive in the presence of esterase. For example, 100 µg/mL of lipoteichoic gives a signal equivalent to about 1 fluorescence unit in the absence of esterase and a signal equivalent to about 4.8 fluorescence units in the presence of esterase. This type of assay may be useful with colored test solutions, for example, blood samples.

Example 8

Lipoteichoic Acid Reactive Material in Crude *Limulus Amebocyte* Lysate

Example 4 shows that lipoteichoic acid reactive material can be harvested from calcium ionophore permeabilized *Limulus polyphemus* hemocytes. This example demonstrates that lipoteichoic acid reactive material is also present in crude *Limulus polyphemus* hemocyte lysate.

Briefly, *Limulus amebocyte* lysate was prepared as originally described in Levin et al. ((1968) supra). The lysate was assayed for the presence of lipoteichoic acid reactive material as described in Example 2. The results indicate that crude *Limulus amebocyte* lysate can detect the presence of lipoteichoic acid in a sample. It is interesting that as the concentration of the crude lysate in the sample mixture is decreased, the signal increased. These results suggest that crude *Limulus amebocyte* lysate contains an inhibitor for the pro-phenol oxidase cascade. However, it appears that the inhibitor can be titrated out so that the crude lysate can detect the presence of lipoteichoic acid in a sample. Accordingly, it appears that the crude *Limulus amebocyte* lysate can detect Gram positive bacteria. Furthermore, it appears that the crude lysate, under the appropriate conditions can detect the presence of Gram positive bacteria (via the pro-phenol oxidase cascade), Gram negative bacteria (via the Factor C cascade) and yeasts and molds (via the Factor G cascade).

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

INCORPORATION BY REFERENCE

All publications and patent documents cited in this application are incorporated by reference in their entirety for all purposes to the same extent as if the entire contents of each individual publication or patent document was incorporated herein.

What is claimed is:

1. A method of producing a preparation for detecting the presence and/or quantity of lipoteichoic acid in a sample, the method comprising the steps of:
    (a) providing a crustacean hemocyte preparation, wherein the crustacean hemocytes in the preparation (i) have an outer membrane and (ii) contain lipoteichoic acid reactive material disposed therein;
    (b) rendering the outer membrane of at least a portion of the crustacean hemocytes in the crustacean hemocyte preparation permeable to the lipoteichoic acid reactive material so that the lipoteichoic acid reactive material is released from the crustacean hemocytes;
    (c) harvesting the lipoteichoic acid reactive material released from the crustacean hemocytes; and
    (d) determining that the lipoteichoic acid reactive material harvested in step (c) is activatable by lipoteichoic acid such that prophenol oxidase is converted into phenol oxidase when the lipoteichoic acid reactive material is contacted with lipoteichoic acid.

2. The method of claim 1, wherein in step (b), the outer membrane is rendered selectively permeable by exposure to a membrane permeabilizing agent.

3. The method of claim 2, wherein the permeabilizing agent is an ionophore.

4. The method of claim 3, wherein the ionophore is a calcium ionophore.

5. The method of claim 1, wherein the crustacean is selected from the group consisting of *Cancer borealis, Cancer irroratus, Carcinus maenas, Hemigrapsus sanguineus*, and *Limulus polyphemus*.

6. The method of claim 1, wherein the crustacean *Cancer* genus.

7. The method of claim 3, wherein the ionophore is admixed with the crustacean hemocyte preparation to give a final concentration in the range from about 0.1 µM to about 100 µM.

8. The method of claim 7, wherein the ionophore is admixed with the crustacean hemocyte preparation to give a final concentration in the range from about 1 µM to about 10 µM.

* * * * *

UNITED STATES PATENT AND TRADEMARK OFFICE
CERTIFICATE OF CORRECTION

| | | |
|---|---|---|
| PATENT NO. | : 7,968,280 B2 | Page 1 of 1 |
| APPLICATION NO. | : 11/292295 | |
| DATED | : June 28, 2011 | |
| INVENTOR(S) | : Wainwright et al. | |

It is certified that error appears in the above-identified patent and that said Letters Patent is hereby corrected as shown below:

IN THE CLAIMS:

In Column 23, Claim 6, line 9, between "crustacean" and "*Cancer*" insert --belongs to the--.

Signed and Sealed this
Sixth Day of September, 2011

David J. Kappos
*Director of the United States Patent and Trademark Office*